(12) United States Patent
Wexler et al.

(10) Patent No.: US 8,369,941 B2
(45) Date of Patent: Feb. 5, 2013

(54) HIGH DEFINITION IMPEDANCE IMAGING

(76) Inventors: Alvin Wexler, Winnipeg (CA); Patrick Adrian O'Connor, Pinawa (CA); Misty O'Connor, legal representative, Kitchener (CA); Rajen Manicon Murugan, Garland, TX (US); Zhong Zheng, Winnipeg (CA)

( * ) Notice: Subject to any disclaimer, the term of this patent is extended or adjusted under 35 U.S.C. 154(b) by 656 days.

(21) Appl. No.: 12/375,145

(22) PCT Filed: Jul. 27, 2007

(86) PCT No.: PCT/CA2007/001327
§ 371 (c)(1),
(2), (4) Date: Jan. 23, 2010

(87) PCT Pub. No.: WO2008/011716

PCT Pub. Date: Jan. 31, 2008

(65) Prior Publication Data

US 2010/0290675 A1  Nov. 18, 2010

(30) Foreign Application Priority Data

Jul. 27, 2006 (CA) .................................. 2554321

(51) Int. Cl.
*A61B 5/05* (2006.01)

(52) U.S. Cl. .................. 600/547; 600/506; 600/546

(58) Field of Classification Search .................. 600/547; 382/128, 109, 131
See application file for complete search history.

(56) References Cited

U.S. PATENT DOCUMENTS

| | | | | |
|---|---|---|---|---|
| 4,539,640 | A * | 9/1985 | Fry et al. | 600/547 |
| 5,381,333 | A * | 1/1995 | Isaacson et al. | 600/547 |
| 6,167,300 | A * | 12/2000 | Cherepenin et al. | 600/547 |
| 2001/0020128 | A1 * | 9/2001 | Morris et al. | 600/437 |
| 2002/0106681 | A1 * | 8/2002 | Wexler et al. | 435/6 |
| 2006/0293591 | A1 * | 12/2006 | Wahlstrand et al. | 600/423 |
| 2007/0032747 | A1 * | 2/2007 | Hashimshony et al. | 600/587 |

OTHER PUBLICATIONS

International search report for international application No. PCT/CA2007/001327.
Written opinion for international application No. PCT/CA2007/001327.

* cited by examiner

*Primary Examiner* — Tse Chen
*Assistant Examiner* — Joel F Brutus
(74) *Attorney, Agent, or Firm* — Oppedahl Patent Law Firm LLC

(57) ABSTRACT

A method for producing a computationally efficient system that reduces the number of iterations required to generate a conductivity image pattern of a subsurface object, and its attendant conductivity distribution, through a solution to the system of field equations that simultaneously satisfies all of the boundary conditions and conserves internal current flux densities.

22 Claims, 14 Drawing Sheets

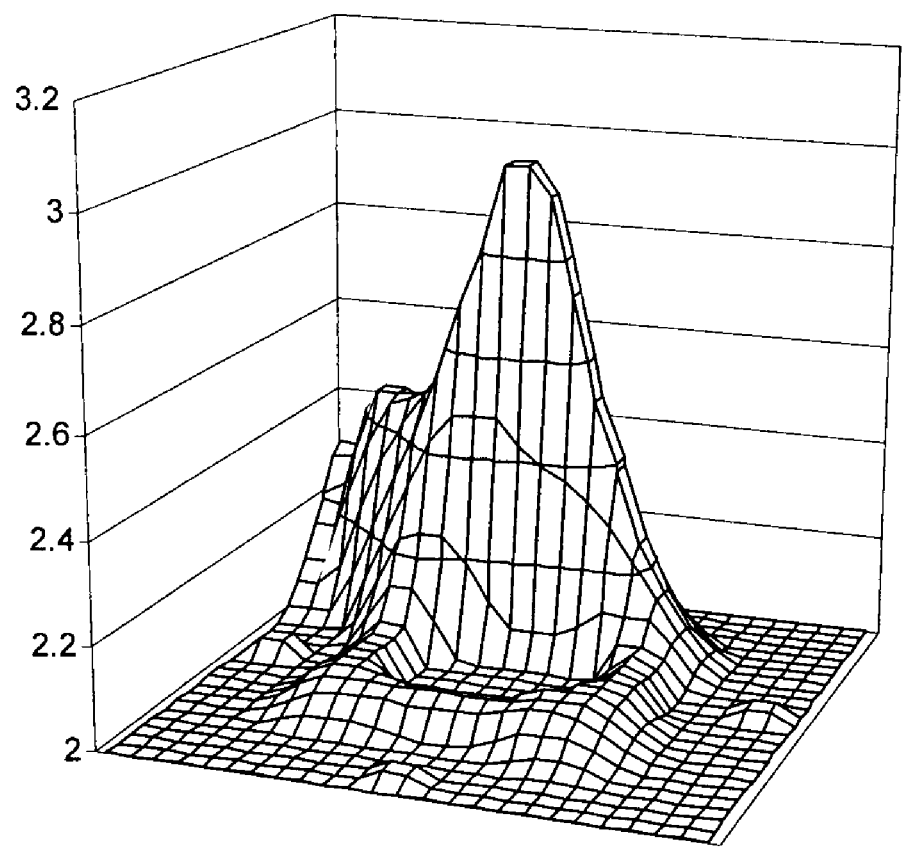
FIGURE 5a  3 excitations

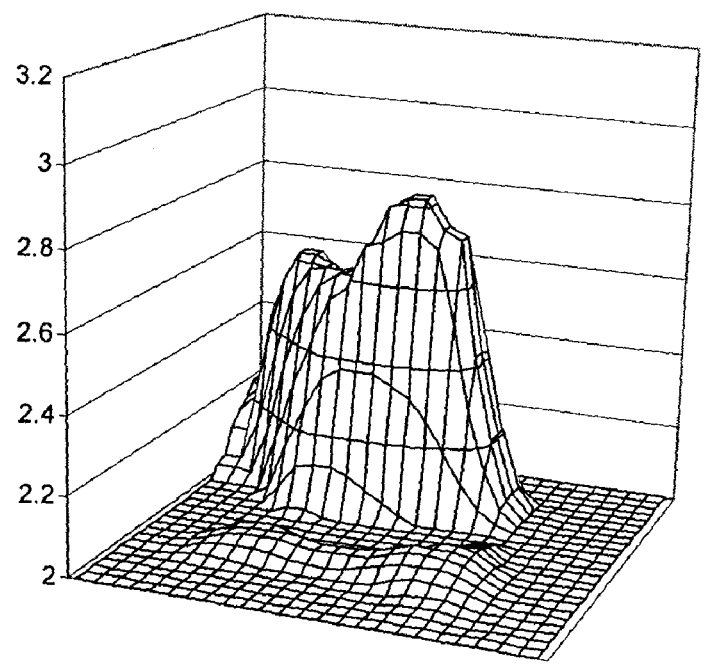
FIGURE 5b 7 excitations

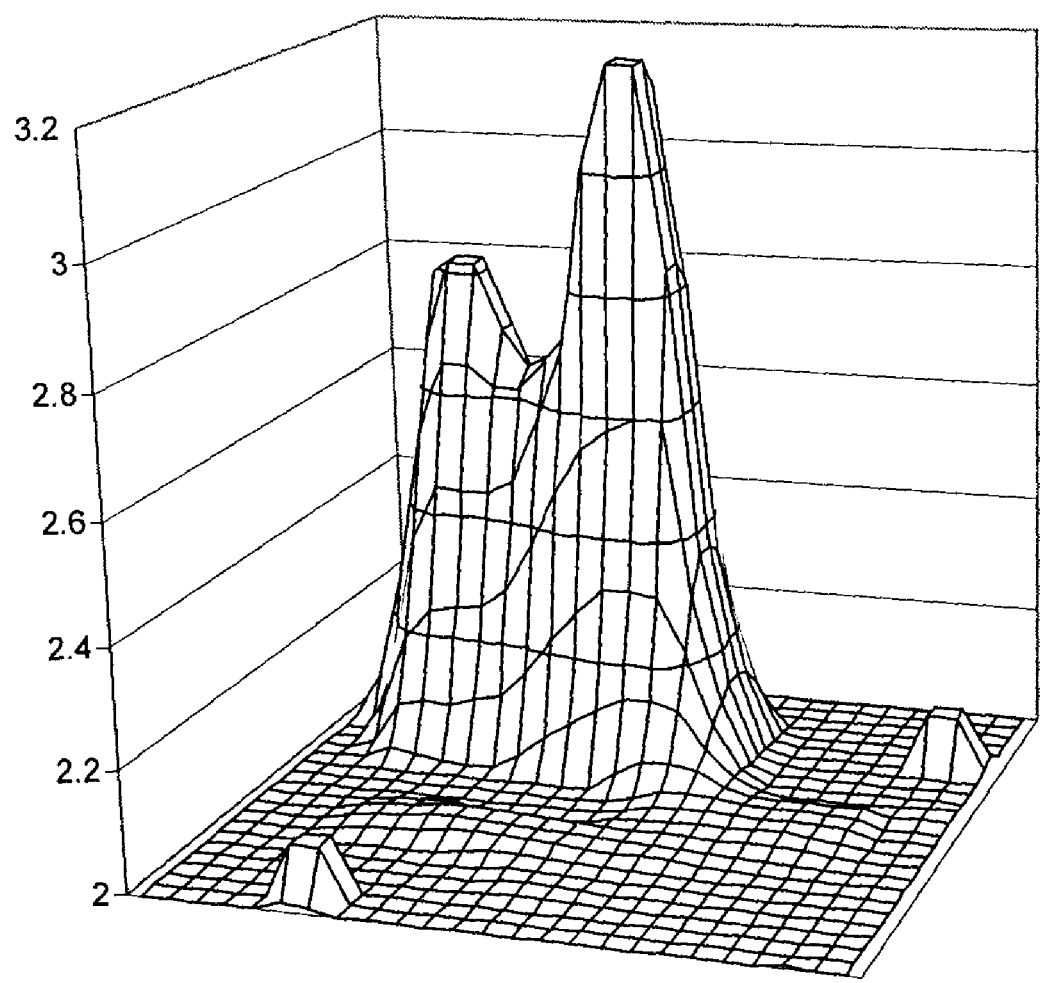
FIGURE 5c  15 excitations

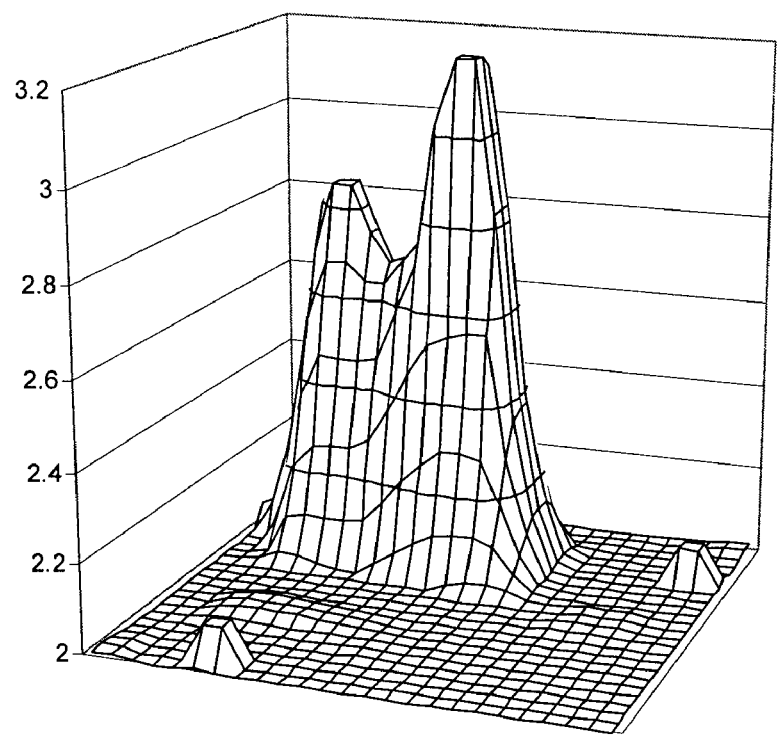
FIGURE 5d 15 excitations with no Gaussian measurement noise applied.

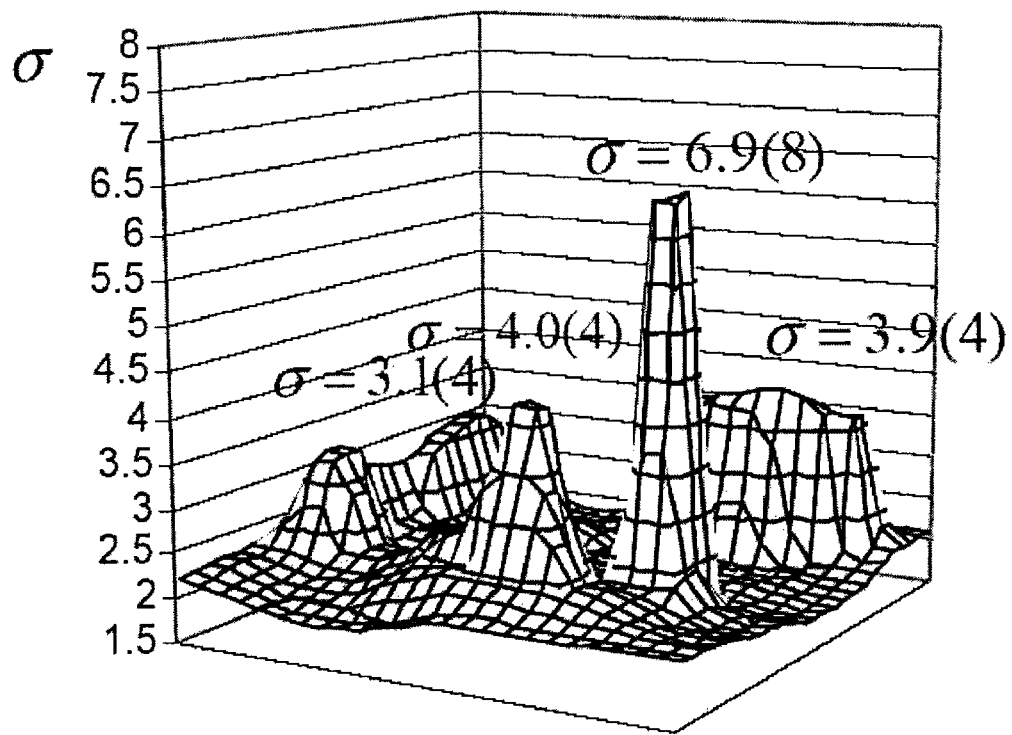
FIGURE 7 Conductivities plotted. Reconstructed conductivities are noted with simulation model values in brackets.

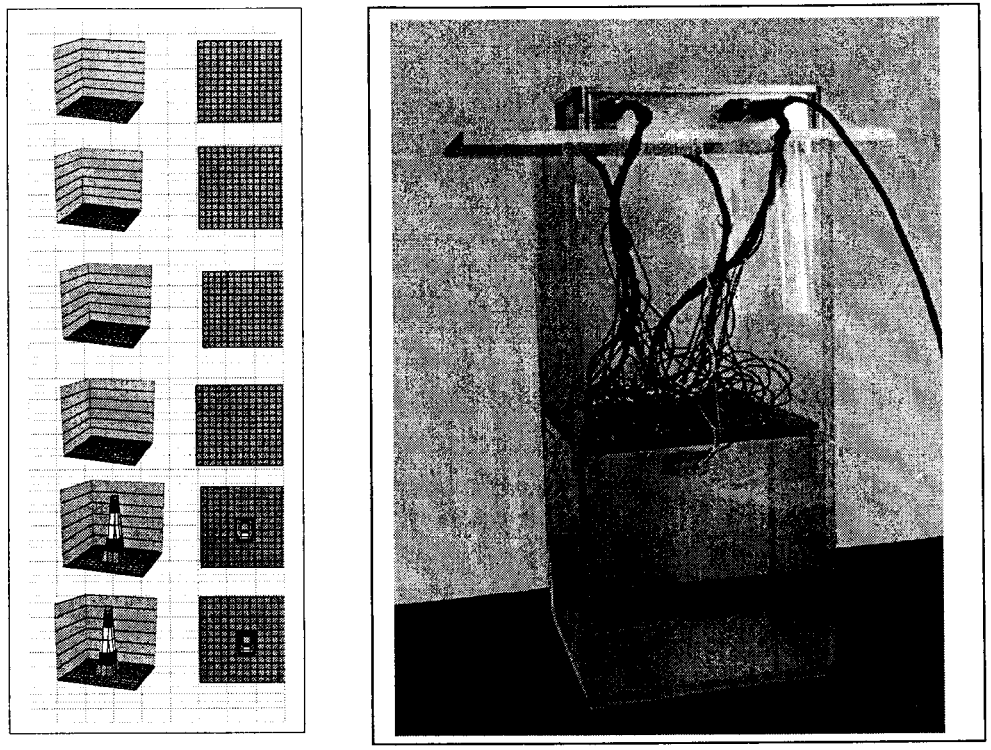
FIGURE 8 Laboratory test setup, using the Threat Detection Group - Canadian Department of National Defence machine, with aluminum-wrapped hockey puck in water. Conductivity plotted in amplitude and with contours at six depth levels.

HIGH DEFINITION IMPEDANCE IMAGING

FIELD OF THE INVENTION

The present invention relates to an improved method and system for detecting and imaging discrete subsurface objects or spatially-continuous inhomogeneous regions within a body which have contrasting conductivity or, more generally, admittivity (i.e. the inverse of specific impedance) within the body. The invention may be used for imaging using electrical currents, sound signals, or other excitations.

BACKGROUND TO THE INVENTION

In a number of disparate technical fields, there has been a constant effort to find improved methods of detecting subsurface objects such as tumours in the human body or land mines underneath the Earth's surface. These methods, known as electrical impedance tomography (EIT), are based upon imaging electrical conductivity or admittivity distributions within a body and generating an image of the subsurface objects based on these electrical conductivity or admittivity values. (The terms "conductivity" and "admittivity" are used interchangeably in the following and it is understood that these terms are the inverses, respectively, of "resistivity" and "specific impedance" or "impedivity").

In biomedical imaging, it is also known that the human body has significant contrasts in electrical conductivity and permittivity (see "Compilation of the Dielectric Properties of Body Tissues at the RF and Microwave Frequencies" by C. Gabriel and S. Gabriel, Technical Report for AFOSR/NL Bolling AFB DC 20332-00014, December 1994-95) and that significant differences exist between biological materials. In cases where the conductivities between materials are similar, the relative permittivities are not and so images can be made to be distinct. Table 1 shows the conductivity and relative permittivity of biological tissues at frequencies of 10 kHz and 100 kHz.

TABLE 1

Conductivity and relative permittivity of biological tissues at frequencies of 10 kHz and 100 kHz

| Tissue | Frequency | Conductivity (S/m) | Relative Permittivity |
| --- | --- | --- | --- |
| Liver | 10 kHz | 0.15 | $5.5 \times 10^4$ |
| Spleen | 100 kHz | 0.62 | $0.326 \times 10^4$ |
| Lung | 10 kHz | 0.11 | $2.5 \times 10^4$ |
| Kidney | 100 kHz | 0.25 | $1.09\text{-}1.25 \times 10^4$ |
| Bone | 10 kHz | 0.013 | $0.064 \times 10^4$ |
| Whole Blood | 100 kHz | 0.55 | $0.40 \times 10^4$ |
| Skeletal Muscle | 10 kHz | 0.55 | $8.0 \times 10^4$ |

One such EIT methodology is disclosed in U.S. Pat. No. 4,539,640 issued to B. Fry and A. Wexler and in a publication by A. Wexler, B. Fry and M. R., Neuman, 1985, "Impedance Computed Tomography. Algorithm and System, "Applied Optics, Vol. 24, No. 23, pp. 3985-3992. The methodology taught by Fry et al. involves the injection of a plurality of electrical signals into a body in time sequence or as multiplex signals through input sites located either upon the surface of the structure or internally thereof, thereby causing current flow along a plurality of paths through each region of the body, which paths terminate in output sites located upon or within the body. At least one characteristic of each signal, such as amplitude, phase or waveform, is measured at a plurality of locations, which are sufficiently removed from the input and output sites. The measured characteristics are compared with the corresponding characteristics of the signal measured at one or more reference points upon or within the structure and the comparison signals obtained are utilized to mathematically reconstruct the spatial relationships between the regions within the structure. An image of the structure interior is then derived from the reconstruction of the aforesaid spatial relationships.

In Fry et al., there is no attempt to restrict the current flow. Rather, the current paths spread and the currents flow throughout substantially the entire region of interest. This general and unrestricted flow of current creates a voltage distribution pattern over the surface or within the region of interest, that may be measured at all sites over or within such region and not just at those active sites through which current is impressed or withdrawn. This surface voltage distribution is a function of the admittivity distribution of the body.

As is known in the art, it is inadvisable to measure voltages at electrodes that are at that moment actively injecting or extracting currents. Such voltage measurements will be influenced by uncertain voltage changes due to uncertain contact resistances. Because there are a large number of voltage measurement sites available that furnish information relative to the interior of the structure, there is little cost in dispensing with the very few, inaccurate voltage measurements taken at current input and output sites. Further, if voltage measurements are taken at high-impedance sites, negligibly small currents are drawn at such sites and, as a consequence, the problem of contact impedance voltage drop is largely avoided because of the solution of the field equations within the three-dimensional region.

The above is a generalization of the four-probe technique disclosed in "Some Observations Concerning Electrical Measurements in Anisotropic Media, and their Interpretation" by Schlumberger, C. and M., and Leonardon, Trans. AIME, Vol. 110, 1934, pg. 159; "Electrical Coring; a Method of Determining Bottom-Hole Data by Electrical Measurements" by Schlumberger, C. and M., and Leonardon, Trans. AIME, Vol. 110, 1934, pg. 237; and "A New Contribution to Subsurface Studies by Means of Electrical Measurements in Drill Holes" by Schlumberger, C. and M., and Leonardon, Trans. AIME, Vol. 110, 1934 pg. 273. Another description of the four-probe technique is described in "Applied Geophysics" by W. M. Telford, L. P. Geldart, R. E. Sheriff and D. A. Keys, Cambridge University Press: London, 1976.

The inclusion of extra equations, resulting from voltage measurements at high-impedance contact sites, permits a reduction in the number of excitations needed for equivalent image quality. This, therefore, reduces the number of computationally costly, three-dimensional field solutions. As a result, the image recovery process is speeded up.

The inverse problem associated with a single excitation configuration, that is the problem of reconstructing from the measured data an image representing the nonuniform distribution of conductivity over a body segment, may not have a unique solution. That is to say, there may be many internal structures that will produce the measured and observed voltage distribution. To reduce the indeterminacy it is necessary to impress a sequence of current-excitation patterns, one pattern at a time or in parallel, for example, by frequency multiplexing. The voltage field distribution is mapped for each case. If sufficient cases are tested, the uncertainty resolves itself to the state where the resultant "pictures" are left with a fuzzy outline. Increasing the number of measurements will improve the "focus" (following the photographic analogy). The measurements are made automatically, for example, using signal-averaging procedures. The data is then stored for subsequent computer analysis.

Fry et al. teaches that given a set of input signals, a computer may be used to "develop" an image of the body and the object located within the body. This is done by finding an internal conductivity distribution within the three-dimensional body that best satisfies, in an average sense, the plurality of measured voltage distribution patterns that result from the sequence of current-excitation patterns, in an iterative fashion. To do the analysis efficiently, a numerical method, such as the finite-difference or finite-element method is used, to produce an efficient solution to the resulting very large systems of equations.

The problem with the methodology disclosed in the Fry et al. patent and the Wexler et al. (1985) publication is that it requires a large number of field and conductivity iterations to generate the conductivity image pattern through a solution to the system of field equations that simultaneously satisfy all of the boundary conditions. Hence, this renders the methodology computationally inefficient.

Since their publication, several attempts have addressed the problem of computational inefficiency in the methodology disclosed in the Fry et al. patent and the Wexler et al. (1985) publication by using methods to accelerate the evolution of the conductivity image pattern. For example, U.S. Pat. No. 6,201,990 issued to A. Wexler and Z. Mu and U.S. Pat. No. 6,745,070 issued to A. Wexler, Z. Mu, R. M. Murugan and G. S. Strobel (collectively referred to below as the Wexler et al. patents) disclose several methods for accelerating the evolution of the conductivity image pattern, such as peak-detection, multi-step extrapolation and successive overrelaxation.

While these methodologies have achieved a significant reduction in the number of iterations for image recovery, the speed and accuracy for the imaging can be further improved using the methodology of the present invention. The reconstruction of images in a rapid manner is required for fast location and identification of very small objects in a body. The present invention provides an improved methodology, over that disclosed in the Fry et al. and the Wexler et al. patents, which is capable of imaging very small subsurface objects significantly faster than the methods of the prior art while producing an accurate image devoid of spurious effects.

SUMMARY OF THE INVENTION

The present invention seeks to provide a method to be used in conjunction with the Fry et al. methodology in order to produce a computationally efficient system that reduces the number of iterations required to generate a conductivity image pattern of a subsurface object, and its attendant conductivity distribution, through a solution to the system of field equations that simultaneously satisfies all of the boundary conditions and conserves internal current flux densities.

In one embodiment of the invention, the first step in the generation of a conductivity image pattern of a subsurface object is to read from a storage device, measured voltages and current excitations obtained in a manner such as those described in the Fry et al. patent. The next step is to run a prior art methodology, such as the basic methodology disclosed in Fry et al., solving the equation set using, for example, the pre-conditioned conjugate gradient method disclosed in the Wexler et al. patents for a fixed number of iterations. For the first of these iterations, the conductivity of the body may be assumed to be a homogeneous value so that field solutions under Neumann and Dirichlet boundary conditions may be imposed, the field potentials may be solved and an approximation to the conductivity within the body may be estimated.

Once a first estimate of the conductivity distribution of the body is achieved, using the basic methodology described in both the Fry et al. patent and publication, the method of the present invention, hereinafter termed the Successive Point Iterative Overrelaxation (SPIOR) method, is used to accelerate the iterative image recovery process to generate successively more refined estimates of the conductivity distribution of the body.

It should be noted that as in the prior art, the region of the body to be imaged is represented mathematically as a plurality of finite elements also referred to as volume pixels (voxels). In its simplest form, each finite element or voxel is represented as a 3-dimensional cube and has a node defined at each of its vertices. The conductivity of the body is defined within each voxel and the electric potential is calculated at each node.

The SPIOR method involves the recalculation of the conductivities of all voxels in proximity to a given node of a given voxel each time the given node voltages are updated, consistent with Neumann and Dirichlet boundary conditions for all excitations. The process involves the iterative repetition of the following steps:

(a) Select a previously-calculated (not measured) voltage node and solve for its new electric potential values in terms of those potential values connected to adjacent voxels;

(b) Before proceeding to the next voltage node, update the conductivities of all voxels adjacent to this node by employing the voltage fields previously obtained by solving the Neumann and Dirchlet equations (i.e. solved under Neumann and Dirichlet boundary conditions for all excitations).

Using this new set of conductivities and the updated node voltages;

(c) Select another (likely adjacent) voltage node; and (d) Repeat the process.

The benefit of the inventive SPIOR method is that the adjacent Neumann-derived and Dirichlet-derived unknown potentials (also referred to hereinafter as Neumann and Dirichlet voltages) and conductivities sense the updated adjacent changes immediately rather than having to await the conclusion of an entire scan of all nodes of the body. Experimentation has shown that the point-wise iterative SPIOR approach of the present invention reduces the total-system iteration count by two orders of magnitude.

The SPIOR method is a generalization of the successive overrelaxation (SOR) method frequently used for the solution of simultaneous equations. But, in this case, iterative solutions for the distinct physical variables $\phi$ and $\sigma$ are integrated rather than performing the operations for all $\phi$ and then for all $\sigma$ variables separately.

In another embodiment of the invention, a Multi-Acceleration Factor (MAF) methodology may be used to further enhance the image-generation process. This is a methodology for employing several acceleration factors in the course of solution of the fields and conductivities. Small acceleration factors (perhaps underrelaxation, i.e. $\omega_K<1$), applied to the general medium, may be chosen to maintain stability of the nonlinear solution process with greater values (likely $\omega_K>1$) used in the vicinity of regions of rapid image-object evolution.

In another embodiment of the invention, an Excitation Modification for Image Enhancement (EMIE) method may be used to further enhance the image generation process. With identification of an important region, after initial image recovery, more electrical current density may be directed to a general region by rearrangement of excitations and/or by adding new excitations that generally bracket and overlay the region of interest. A weighting factor may also be included to strengthen the influence of certain currents in the region. These actions enhance the image definition and the conductivity evaluation. They may be invoked upon visual inspection, or automatically by means of signature identification of biological lesions, landfill effluent, landmines, etc.

In still another embodiment of the invention, a Locator-Compensator (LC) Method may be used to focus attention upon specific regions of interest in order to rapidly evolve the conductivity of these regions. The LC method encloses identified regions within artificial boundaries by applying, as boundary conditions, computed currents and electric potentials. Once the identified regions are enclosed, the SPIOR method is applied exclusively within the identified regions for several iterations. In this way, computational effort is concentrated on subregions that have distinctively large or small conductivities or are experiencing rapid change of conductivity values with iteration. The LC method then returns to the global SPIOR iteration procedure if the computed subregion excitation boundary potentials differ from the applied boundary potentials by a significant amount as determined by an error norm. The LC method may be repeated several times if the artificial subregion boundary conditions require iterative correction.

Yet another embodiment of the invention provides a method of impedance imaging of a target region located within a body. This method comprises the steps of:

(a) representing the body as a plurality of adjacent finite elements, each finite element having a plurality of nodes and a distribution of admittivity values at a set of pre-defined points therein;

(b) applying at least one excitation, at at least one selected excitation input means, to flow within the body and exit therefrom at at least one selected excitation output means;

(c) measuring at least one characteristic at the or each of at least one selected characteristic measurement means;

(d) identifying a measured characteristic group of nodes as comprising those nodes corresponding to the at least one selected characteristic measurement means;

(e) identifying a volume comprising a first one of the finite elements and those finite elements defining a region thereround;

(f) calculating at least one first characteristic value, for each node that lies within the volume and outside the measured characteristic group of nodes from the measured characteristic at the measured characteristic group of nodes;

(g) calculating at least one second characteristic value for each node that lies within the volume from the distribution of admittivity values and the at least one excitation;

(h) deriving an excitation value corresponding to each pre-defined point within the volume from the corresponding distribution of admittivity values and the at least one second characteristic value;

(i) updating the distribution of admittivity values corresponding to the set of pre-defined points within each finite element within the volume from the corresponding excitation value, the at least one first characteristic value and the measured characteristics at those of the measured characteristic group of nodes that lie within the volume; and (j) displaying an image of the target region using the distribution of admittivity values within the body.

BRIEF DESCRIPTION OF THE FIGURES

FIGS. 5a, 5b, 5c and 5d show conductivity amplitude plots generated by an embodiment of the present invention employing the Multi-Acceleration Factor Methodology and Excitation Modification for Image Enhancement and shows the small effect of measurement noise.

FIG. 7 shows conductivities recovered with simulation model values using one aspect of the invention.

FIG. 8 illustrates a laboratory test setup used in testing aspects of the invention.

DETAILED DESCRIPTION OF THE INVENTION

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

Figure 1:
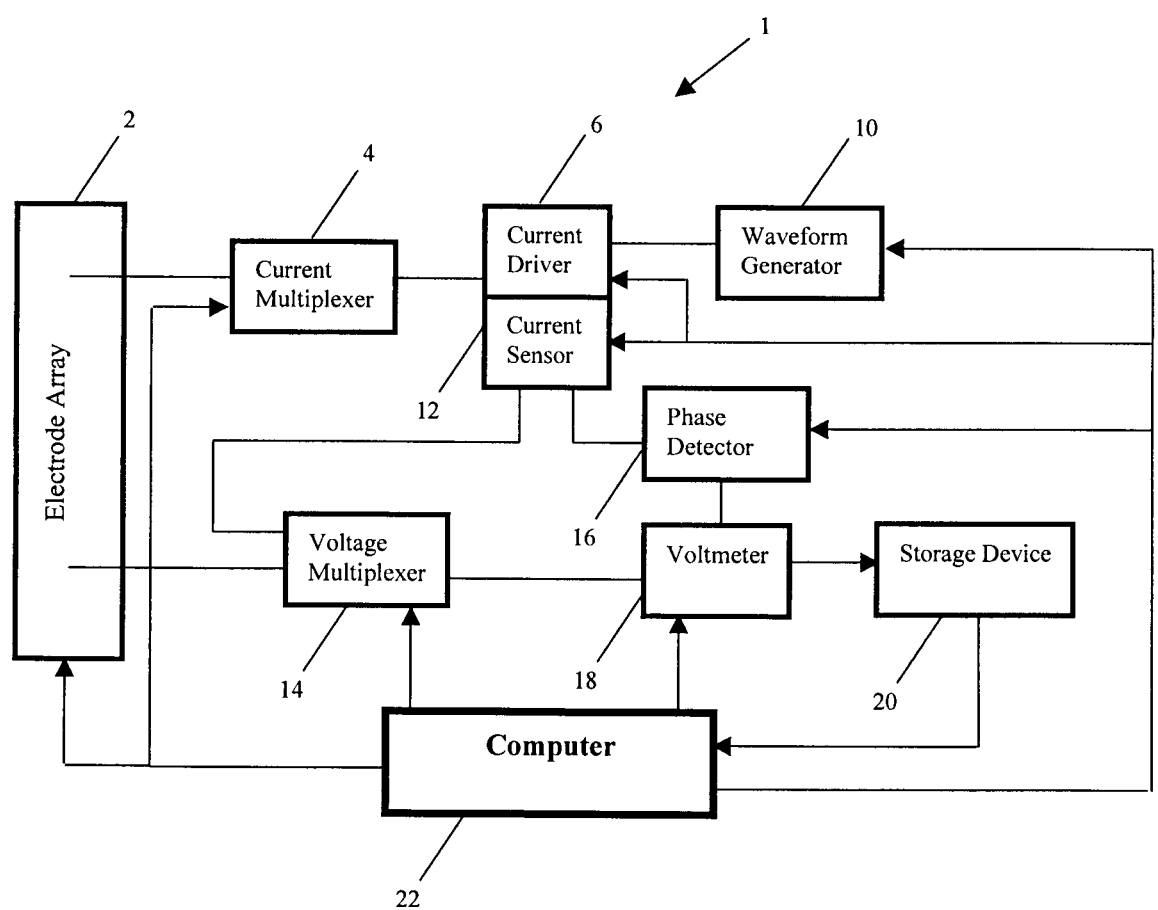
FIG. 1 is a block diagram of the system according to an embodiment of the present invention.

In FIG. 1, there is shown a block diagram of a system 1 according to an embodiment of the present invention. The system 1 comprises an electrode array 2 for placement on or around the medium such as a human body or a subterranean region of the earth's surface within which an object to be imaged is located. The electrode array 2 includes a plurality of current electrodes (not shown) used to inject (source) current into the medium and a plurality of current electrodes (not shown) used to extract (sink) current from the medium. The electrode array 2 also includes a plurality of voltage electrodes (not shown), which measure the surface voltage of the medium.

Each current electrode (not shown) of the electrode array 2 is operatively coupled to a current multiplexer 4, which in turn is operatively coupled to a current driver 6. A waveform generator 10 is operatively coupled to the current driver 6. A person of ordinary skill in the relevant art will readily recognize that multiple multiplexers and multiple current drivers may be used instead of one multiplexer with a single current driver to operate the current electrodes in parallel.

Each voltage electrode (not shown) is operatively coupled to a single voltage multiplexer 14 which in turn is operatively coupled to a voltmeter 18. The voltmeter 18 is operatively coupled to a storage device 20. The storage device 20 is in turn operatively coupled to or may be included in a computer 22. The computer 22 is operatively coupled to the current multiplexer 4, the current driver 6, the waveform generator 10, the current sensor 12, the phase detector 16, the voltmeter 18, so that it can control the operation of the system 1.

In operation, the computer 22 selects the current electrodes through which current is to be injected into the medium and also selects the current electrodes where the current is to be extracted from the medium. In order to inject current into the medium, the computer 22 transmits a control signal to the waveform generator 10 which generates a voltage signal of the waveshape and frequency set by the computer 22. The current driver 6 produces a current signal, proportional to the signal from the waveform generator 10, at an amplitude set by the computer 22. The current driver 6 is coupled to the selected source and sink current electrodes (not shown) through the current multiplexer 4. The current sensor 12 produces a voltage proportional to the current for measurement by the voltmeter 18, and provides a signal to an optional phase detector 16 that permits the voltmeter 18 to make measurements of the voltages and currents and optionally their relative phase relationship.

The computer 22 controls the voltage multiplexer 14 to sequentially select the voltage electrodes at which the voltage should be measured. The selected voltage electrodes are connected to the voltmeter 18 which measures the voltage between the selected voltage electrodes. The computer 22 controls the current multiplexer 4 to inject the preset currents through a sequence of current electrodes and to make a sequence of voltage measurements by the voltage multiplexer 14 and voltmeter 18 in a programmed sequence.

The current injected through the selected electrodes flows through the entire medium containing the object to be imaged, thereby creating a voltage distribution pattern throughout the medium and over the surface of the medium. This voltage distribution, which is a function of the impedance distribution of the medium is measured using the voltage electrodes selected by the computer 22 via the voltage multiplexer 14. These voltage measurements, along with the injected and the withdrawn current (hereinafter "excitations"), are transmitted to the storage device 20. The computer 22 retrieves these excitations and then proceeds to generate an image of the subsurface object using the processes described in U.S. Pat. No. 4,539,640 issued to Wexler et al. and "Impedance Computed Tomography, Algorithm and System", Applied Optics, Vol. 24, No. 23, pp. 3985-3992, in conjunction with the inventive methodology described below, which we denote Successive Point Iterative Overrelaxation (SPIOR).

It should be noted that the electrode array 2 may be made in several forms. In one embodiment of the invention, the electrode array 2 comprises a plurality of electrodes that are applied directly to the surface of a body. In another embodiment, the plurality of electrodes may be electrically connected to the surface of the body via a conductive fluid, as described in U.S. Pat. No. 4,486,835 issued to Bai. In still another embodiment, the electrode array 2 may be a flexible printed circuit board array of physiological electrodes with conductive gel arranged in a specific arrangement for direct application to the surface of the body. In yet another embodiment, the electrode array 2 may include electrodes attached to a plate, which are to be applied to a surface to be imaged. In another embodiment, some of the electrodes may be embedded into the medium within the enclosing surface or the walls of the enclosing medium may be printed circuit boards in which the pads (to which components are normally affixed) function as electrodes.

Once the excitations have been measured and stored in the storage device 20, the computer 22 generates an image of the subsurface object using an iterative process involving successive estimates of potential and conductivity. The process begins with the prior art methodology described in the Fry et al. patent and publication, which we denote the Basic Methodology, to start the imaging of the subsurface object.

The Basic Methodology

The Basic Methodology finds the solution to the electromagnetic field equations that govern current flow within a body being imaged. Physically, the current flow within the body induces an electrical potential that is a function of the conductivity of the body. The relationship of this electric potential to the impressed current distribution is defined by the Poisson equation $$-\nabla \cdot \sigma \nabla \phi = f \quad (1)$$

where $\sigma$, $\phi$ and $f$ are the conductivity, electrical potential (i.e. voltage) and impressed current source distributions respectively within the region being studied, having respectively units of measurement of $(Ohm\text{-}m)^{-1}$, volts and Amperes/$m^3$.

Equation (1) is subject to Neumann and Dirichlet boundary conditions, which are $$-\sigma(s)\frac{\partial \phi}{\partial n}\bigg|_s = h(s) \quad (2a)$$

and $$\phi(s) = g(s) \quad (2b)$$

respectively, where h(s), in Amperes/$m^2$, describes the electrical current flux density entering or leaving the medium over an electrode surface.

The function $f$ denotes the impressed currents within the region in addition to the currents impressed at the surface boundary defined in 2(a). If no current is impressed at the surface boundary, h(s)=0. In the above equations, $\phi(s)=g(s)$ corresponds to the measured potential (in Volts) over the surface where g(s) represents the voltage distribution, measured over the surface, at electrode sites. It should be noted that g(s) may also represent the voltage distribution at all points along a conducting surface that is attached to a measured or otherwise known voltage site. These voltage values are applied in the Dirichlet solution as part of the solution process for the conductivity distribution. In general, $g(\bar{r})$ represents the impressed or otherwise known point-source and/or continuous voltage distributions anywhere within the region. The symbol n represents the direction normal to the surface.

It should also be noted that although equations (2a) and 2(b) strictly apply to the d.c. case, it may be assumed to be applicable to the a.c. case and to include dielectric and magnetic media effects. Those having ordinary skill in this art would readily be able to replace conductivity with conductivity and permittivity and permeability, at higher frequencies, to deal with the complex admittivity using complex arithmetic in place of the real numbers otherwise used in the arithmetic. In the following discussion, the term "conductivity" should be understood to include the more general concept of complex admittivity.

Equation (1) is applied in turn to each pair of Neumann and Dirichlet solutions for each excitation pattern. However, with boundary conditions corresponding to actual measurements and with the conductivity being only an estimate of what actually existed during the measurement, the pair of boundary conditions in equations 2(a) and 2(b) applied to the solution cannot be expected to produce identical computed internal fields. The imposition of Ohm's Law $$\bar{J} = -\sigma \nabla \phi \quad (3)$$

where $\bar{J}$ represents the current density throughout the interior region employing the previously estimated current flow density $\bar{J}$ derived from the Neumann problem and $\nabla\phi$, in which the potential $\phi$ is derived from the Dirichlet problem, for all excitations, permits a conductivity distribution to be found that yields approximate compatibility with the given Neumann and Dirichlet boundary conditions. Equation (3) therefore supplies a constraint that links the Neumann and Dirichlet solutions.

To this end, a least-squares technique is employed to produce an improved estimate of the conductivity distribution that satisfies both boundary conditions, for all excitations, in an average sense. This causes a displacement to the value of the conductivity estimate.

With the current density (as calculated from the potential distribution using the Neumann boundary condition of Equation 2(a) throughout) and the potential (as calculated using measured voltages applied, i.e. the Dirichlet boundary condition of Equation 2(b) where appropriate), Ohm's law is generally not satisfied. Thus, there is a residual wherever it is evaluated.

To enforce compatibility, the minimization of the square of the residual over all points and for all excitations is sought. It is therefore sought to minimize $$R = \sum_X \int \int_V \int (\bar{J} + \sigma \nabla \phi) \cdot (\bar{J} + \sigma \nabla \phi) dv \qquad (4)$$

where R is the squared residual sum of the lack of conservation of current density in the use of the Neumann and Dirichlet boundary conditions, v is the region over which the imaging is performed, and X represents the excitations over which the sum is taken.

If both conductivity and permittivity are considered (i.e. admittivity), the complex conjugate of the second bracketed term is taken and the following equations are appropriately amended. Thus Equation (4) can be represented as a summation over finite element volumes (or voxels), $$R = \sum_X \sum_j \int \int_{V_j} \int (\bar{J} + \sigma_j \nabla \phi) \cdot (\bar{J} + \sigma_j \nabla \phi) dv \qquad (5)$$

Then, to minimize the residual by adjustment of each conductivity value $\sigma_i$, we take $$\frac{\partial R}{\partial \sigma_i} = 0 \qquad (6)$$

in which $\bar{J}$ and $\phi$ are held at previously computed values. A person of ordinary skill in the art will readily recognize that if permittivity is also considered, then the derivative with respect to permeability must also be evaluated. Rearranging the equation gives $$\sigma_i = \frac{-\sum_X \int \int_{V_i} \int \bar{J} \cdot \nabla \phi dv}{\sum_X \int \int_{V_i} \int \nabla \phi \cdot \nabla \phi dv} \qquad (7)$$

In effect, this formulation has cast the error term into the interior affording local control rather that at a distance. It turns out that the resulting equation set is not ill-conditioned.

Note that (7) is analogous to the lumped network equivalent $G=IV/V^2=I/V$, i.e. Ohm's law!

Several numerical methods may be used to accomplish the above operations in Equation (7) consisting of a solution of two sets of voltage potential fields for each excitation (i.e. one with the Neumann boundary condition of Equation 2(a) and the other with the Dirichlet boundary condition of Equation 2(b) applied where appropriate) followed by the evaluation of an estimate of the conductivity distribution.

The Basic Methodology uses the Finite Element Method (FEM). (The Finite Difference Method (FDM) may also be used.) In its simplest form, one may assume a constant a value within each element i. However, the algorithm provides for inhomogeneous and orthotropic conductivity values. If the conductivity is allowed to vary within each element, the conductivity value would need to be evaluated at several points within each element and the necessary higher-order finite elements would require more than eight nodes for voltage distribution definition. Equation (7) results in a very sparse matrix operation as a result of using the Finite Element Method over the interior. In contrast, attempting to match the measured and computed boundary potentials by optimization of the interior voxel conductivities produces unwieldy and dense matrices and ill-conditioning. Sparse matrices permit a great number of variables to be managed. In this case, this means that one is able to deal with small voxels, thus yielding high definition imaging on the condition that the number of $\sigma_i$-updating iterations is not large.

As this is a nonlinear system, the solution of compatible potentials and conductivities is accomplished through an iterative sequence of computations. The above operation (7) yields a new conductivity value within the region of each element i. Equation (7) is applied over all points at which the conductivity $\sigma_i$ is desired. With this new set of conductivity values the operation is repeated: new field distributions are calculated from the new conductivity distribution using Equation (1) and, consequently, a new set of conductivities is determined from the new field distributions, for all excitations, using Equation (7).

To provide a stopping criterion for the iterative process, the following interior residual norm may be used:

$$\frac{\|R\|}{\|\bar{J}\|} = \left[ \sum_X \sum_j \int \int_{V_j} \int (\bar{J} + \sigma_j \nabla \phi) \cdot (\bar{J} + \sigma_j \nabla \phi) dv \bigg/ \sum_X \sum_j \int \int_{V_j} \int \bar{J} \cdot \bar{J} dv \right]^{1/2} \qquad (8a)$$

Alternatively, the boundary error norm $$\|E\|/\|\phi_{measured}\| = \|\phi_{measured} - \phi_{calculated}\|/\|\phi_{measured}\| \tag{8b}$$

may be used. Alternatively, both the interior residual norm and the boundary error norm may be used to provide a stopping criterion.

These norms are tracked and when it is apparent that a minimum has been reached, and the norms are not beginning to increase, the iterative process is discontinued. Alternatively, when one or more of these norms begin to increase due to the onset of non-convergence, the iterative process may be discontinued. As another alternative, values for these norms may be used to exit from the procedure once calculated norms become less than the exit norms.

It should be noted that, as in all impedance tomography methodologies known in the art, one may employ filtering techniques in order to suppress the growth of artefacts. Otherwise, false patterns arise and the use of the above norms, to judge when acceptable convergence has been achieved, will be unreliable. The present invention utilizes the filtering principles described in "Computer Implementation of Image Reconstruction Formulas", by S. W. Rowland, Chapter 2, pp. 9-79 and "Image Reconstruction from Projections—Implementation and Applications" by Ed. G. T. Herman, *Topics in Applied Physics*, Vol. 32, Springer-Verlag, Berlin, 1979.

The present invention may use any one of two filtering methods, known as median filtering and weighted averaging filtering. In both filtering methods, the conductivities of the voxels in immediate proximity to a node are selected. For median filtering, the median value is selected as the conductivity value. This eliminates spikes that appear with dimension of one voxel and preserves the edge shapes. The averaging filter simply averages the conductivity values in proximity to the voxel in question.

The inventive SPIOR scanning through a fine mesh carries with it accumulating error that is deposited in the vicinity of the far end of the scan. This accumulation of error appears to be the cause of artefact generation. Alternately reversing the scan direction has a corrective benefit due to the input of the boundary conditions. More generally, the scan direction can be initiated from various boundaries in turn.

In summary, Equation (8a) is a measure of the violation of conservation of current density and Equation (8b) is a measure of disagreement between measured and calculated voltage values.

The problem with the above Basic Methodology is that a large number of iterations are required to achieve convergence in order to generate an image of the subsurface object. This consequently results in lengthy computation times. To accelerate the image generation process, the image computer 22 uses the method of the present invention, hereinafter termed Successive Point-Iterative Overrelaxation (SPIOR), in conjunction with the basic methodology and several other procedures.

Successive Point Iterative Overrelaxation (SPIOR) Method

Until now, all of these calculations have been described in the Fry et al. and/or in Wexler et al. patents.

Figure 2:
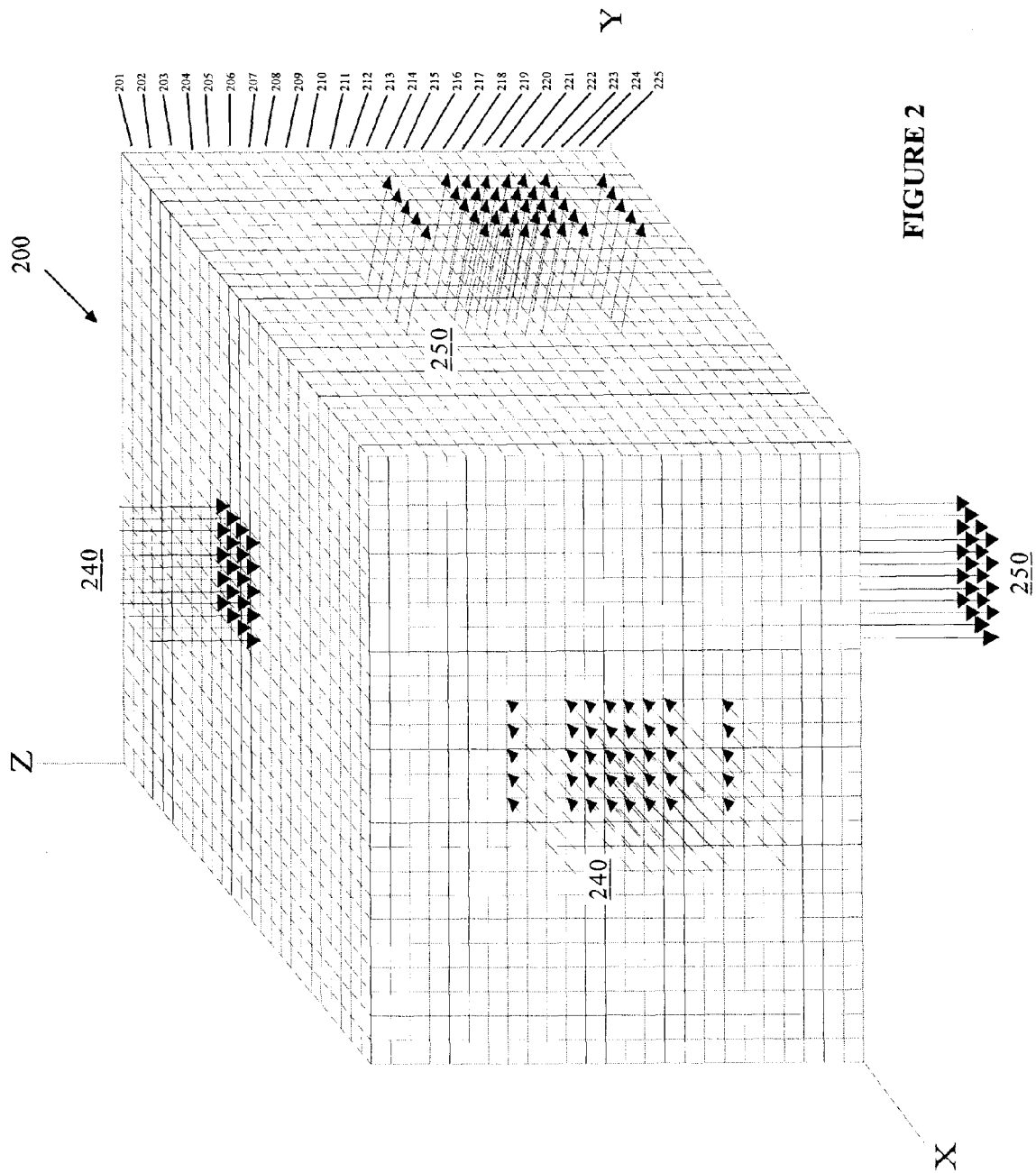
FIG. 2 shows a cube which represents a region within which an immersed body would be imaged by the method of the present invention.

The inventive SPIOR methodology used to accelerate the generation of an image will now be described by an example and with reference to FIGS. 2 and 3. Referring to FIG. 2, a region within a body 200 to be imaged has a plurality of 3-dimensional cubes, known in the art to be finite elements, distributed over a plurality of layers 201, . . . , 225. The cube 200 shows two areas where current is input 240 into the region and drawn 250 from the region by current electrodes (not shown). It should be noted that the electrodes may be located arbitrarily within the region, that is they all may be placed upon the top surface alone, they may be distributed over all surfaces or the electrodes may be located within the body of the region. For the purpose of explanation, this example of the SPIOR methodology begins by assuming that all applied currents and measured voltages are located at outer surfaces of the region shown in FIG. 2.

Figure 3:
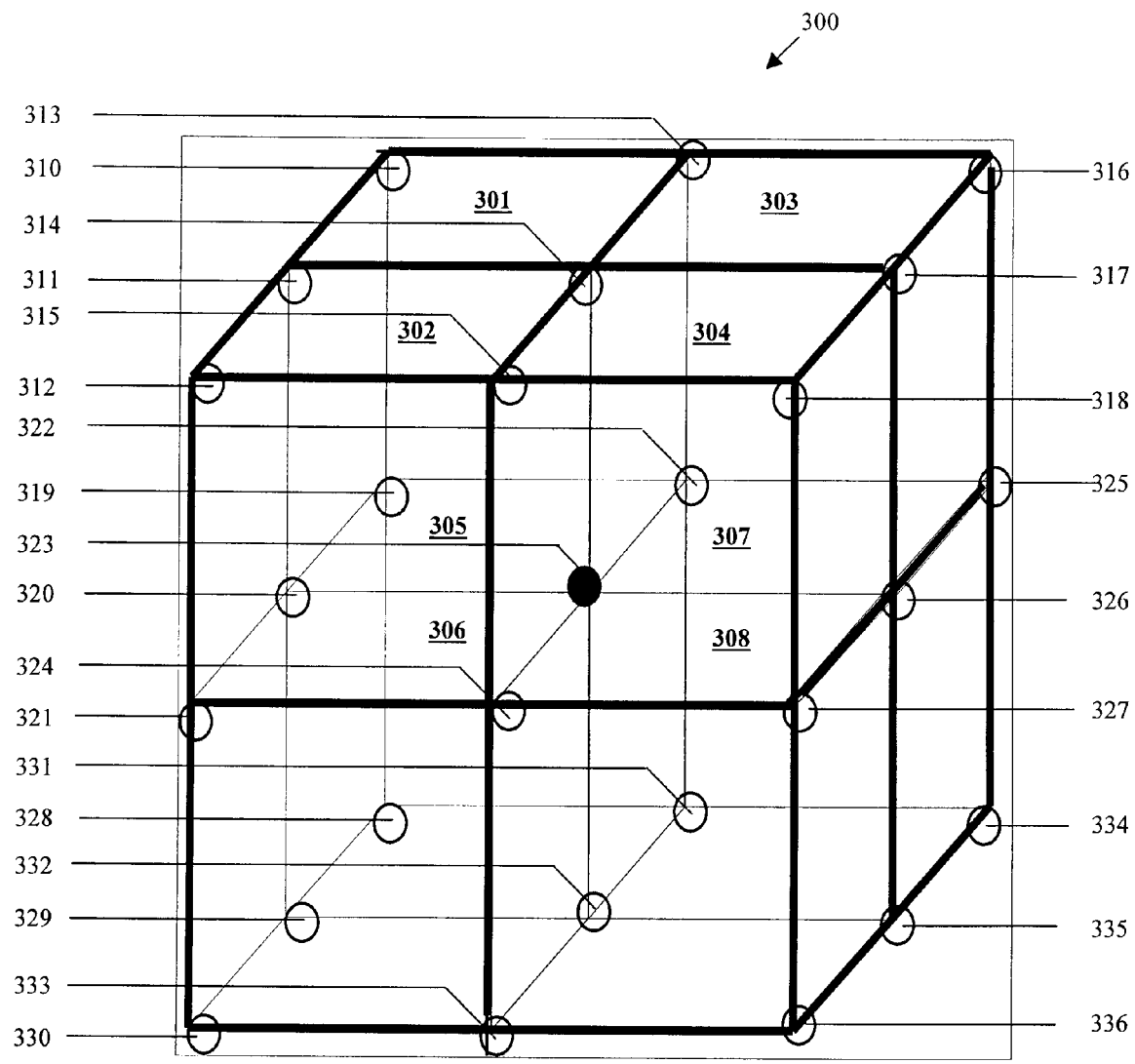
FIG. 3 shows a sub-region of the imaging region shown in FIG. 2.

FIG. 3 shows a sub-region 300 of FIG. 2 which contains 8 lower-order finite elements. As is known in the art, a lower-order finite element is one which has a constant conductivity within the cube and a node at each vertex of the cube. With this defined finite element structure, there is approximately, on average, one node per finite element. Referring to FIG. 3, the sub-region 300 has 8 finite elements 301, 302, 303, 304, 305, 306, 307, 308 (indicated at the top surface of each finite element) surrounding a central node 323 whose Neumann and Dirichlet solutions voltage values are to be computed, as part of an iterative procedure, as a function of the voltages at the other 26 nodes (excluding node 323) 310, . . . , 336 where the voltage values are assumed to be known. In the estimation of the node voltages at 323, no other nodes are used. The values of the conductivity within each of the finite elements 301, 302, 303, 304, 305, 306, 307, 308 and the 27 potentials at the nodes 310, . . . , 336 of each of the finite elements are represented mathematically in a matrix system of the form $$A\underline{x} = \underline{b} \tag{9}$$

Referring again to FIG. 2, the region 200 contains 25 finite elements along each edge for a total of 15,625 finite elements. Depending on the number of measured voltages, there are perhaps 15,000 unknown voltages and so this will be roughly the voltage matrix order (number of rows) for each three-dimensional Neumann and Dirichlet field solution. There are 27 nonzero entries per matrix row and so these nonzero entries constitute 405,000 entries out of 225 million matrix locations, resulting in a matrix density of approximately 0.18 percent. This low density calls for the use of sparse matrix methods for storage and computation. In effect, by casting the norm minimization problem into the interior of the region, instead of using boundary norm minimization with the resulting dense matrices, sparse matrix methods are applicable.

The operation of present invention may now be described using the exemplary FIGS. 2 and 3. Remaining at the node 323, the node potential values (one for each Dirichlet and Neumann excitation pattern), are updated based on the current values of the node potentials at the other 27 nodes, 310, . . . , 336 and the conductivities of the eight adjacent finite elements 301, 302, 303, 304, 305, 306, 307, 308. Next, the conductivities of the eight adjacent finite elements 301, 302, 303, 304, 305, 306, 307, 308 are updated using Equation (7) noted above. Because the number of measurements, resulting from the linearly independent excitations typically exceeds the number of unknown $\kappa_i$ conductivity values, a three-dimensional image may be generated using a least-square solution process as there are more equations than unknowns. The potentials and conductivities are treated as part of the same nonlinear system of simultaneous equations which are solved iteratively. Referring to Equation (9) above, this relationship may be expressed as $$\sum_j a_{ij} \chi_j = b_i \tag{10}$$

in which $\chi_j$ represents an electric potential or conductivity value as described above.

Rearranging in order to update the unknowns one at a time, $$\chi_i^{(n+1)} = \frac{1}{a_{ii}} \left( b_i - \sum_{j \neq i} a_{ij} \chi_j^{(n)} \right) \quad (11)$$

where n denotes the iteration count. Applying an acceleration factor, $$\omega(\chi_k^{(n+1)} - \chi_k^{(n)}) + \chi_k^{(n)} \Rightarrow \chi_k^{(n+1)} \quad (12)$$

for each $\chi_k$ in turn 1(1)N where there are N equations allows for the solving of even larger systems with few $\phi$–$\sigma$ iterations. The acceleration factor $\omega$ represents the voltage $\omega_\phi$ or conductivity $\omega_\kappa$ acceleration factor as appropriate. In general, a variety of $\omega_\phi$ and $\omega_\kappa$ values may be used for a variety of peaks and regions.

The acceleration factor $\omega_\kappa$, applied to conductivity calculations over most of the region, may be less than 1 and is then, in fact, an underrelaxation (i.e. $\omega_\kappa < 1$) where this small value of $\omega_\kappa$, e.g. 0.2, is chosen to ensure stable convergence of the nonlinear equation set through the iterative solution process. However, for the acceleration of peak sub-regions, large acceleration factors are beneficial. The result of this SPIOR process is rapid convergence of the sparse nonlinear system, which results in rapid convergence of the system $A\underline{\chi} = \underline{b}$ for high-definition impedance imaging.

Figure 4:
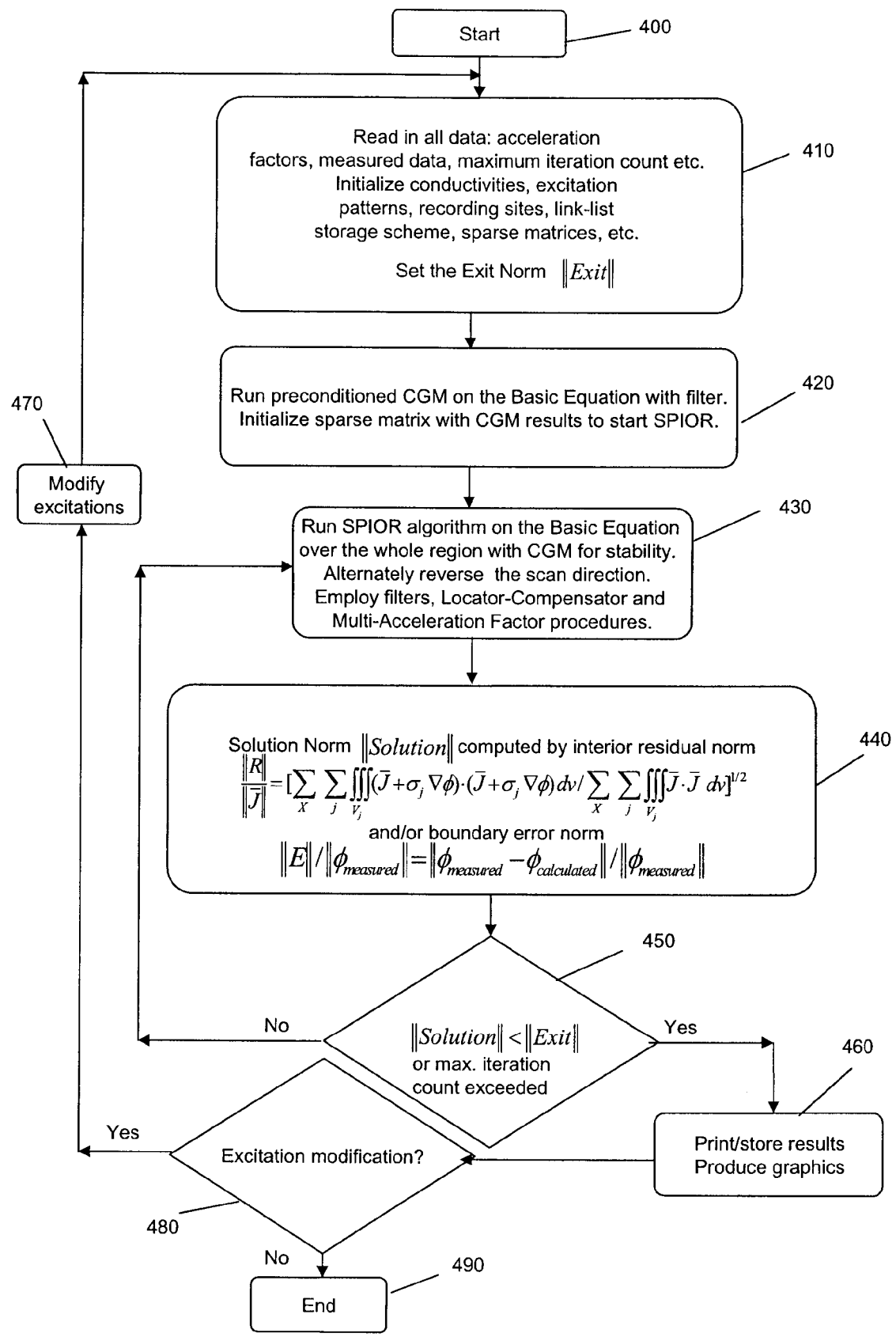
FIG. 4 shows a high-level flowchart of an imaging process of the present invention.
Figure 6A:
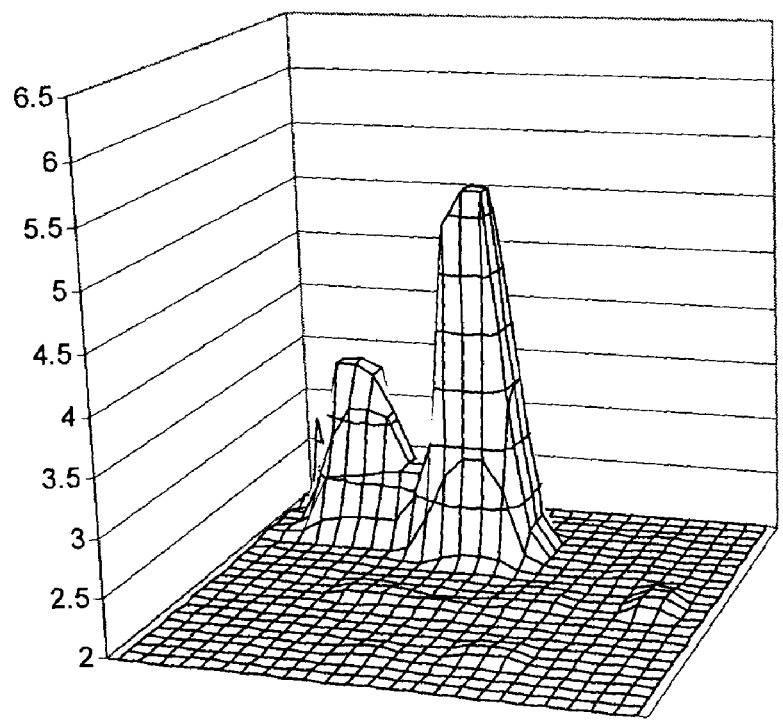
FIGS. 6a, 6b, 6c and 6d show conductivity amplitude and contour plots generated by another embodiment of the present invention employing Excitation Modification for Image Enhancement.
Figure 6B:
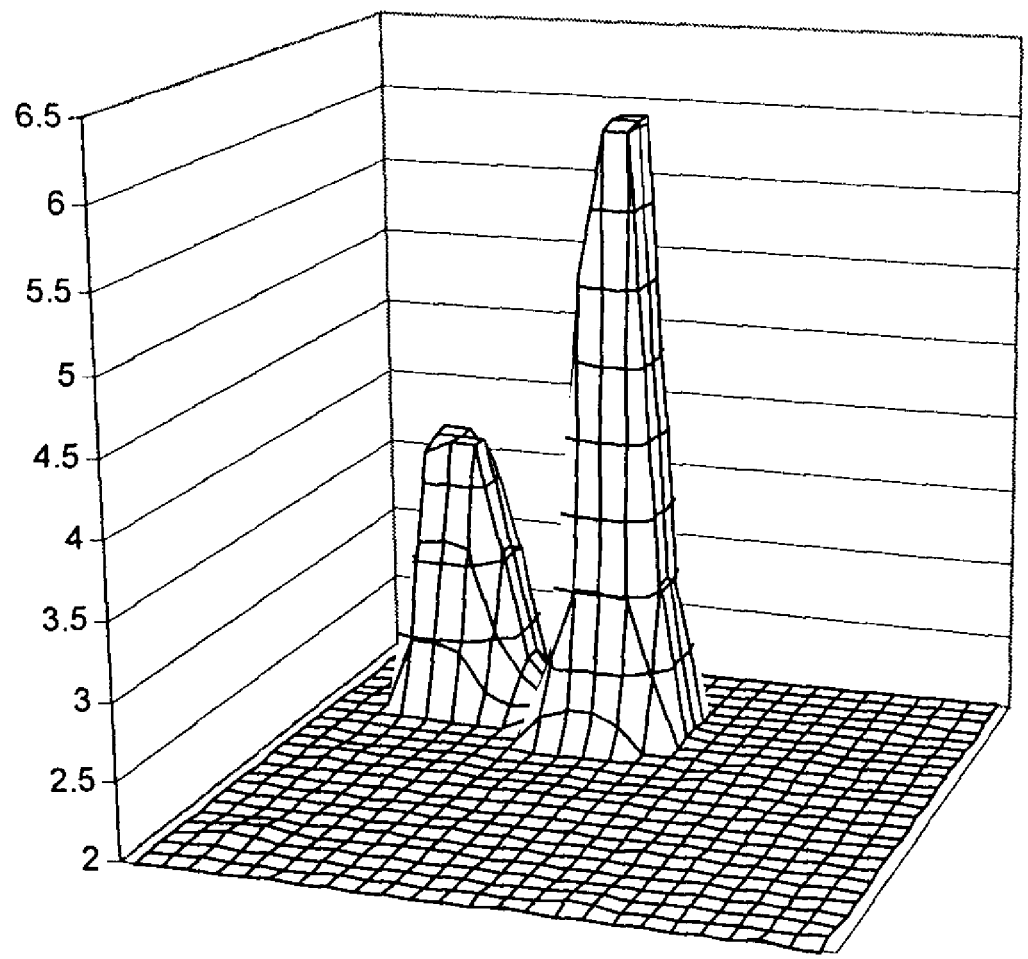
Figure 6C:
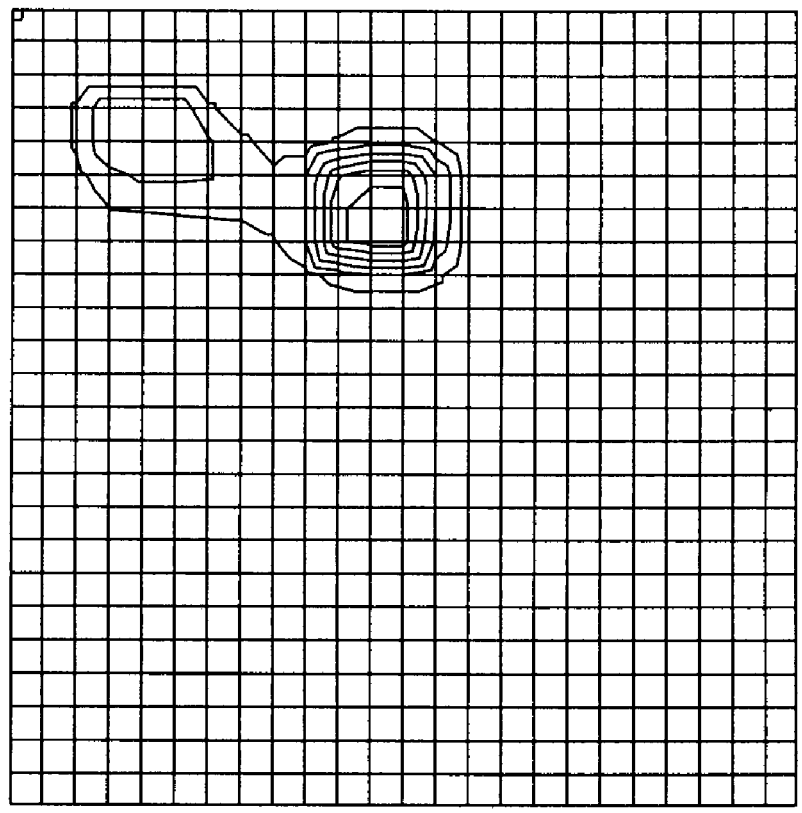
Figure 6D:
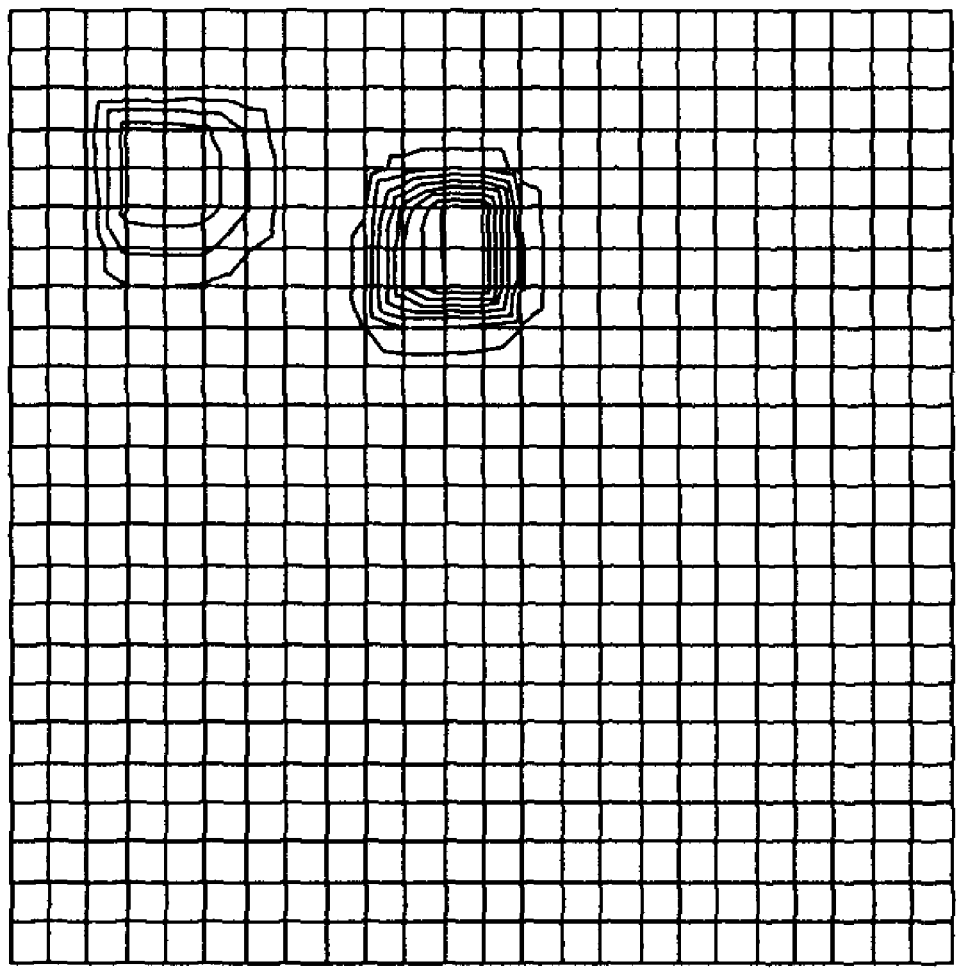

Referring to FIG. 4, a high-level flowchart of the imaging process of the present invention is shown. The imaging process begins at step 400 and then proceeds to step 410 where data such as voltage measurements and excitations are read by the imaging computer 22 from the storage device 20. Also during step 410, the imaging process initializes the conductivities of all the finite elements, sets the exit norm condition and sets that maximum iteration count. The imaging process then proceeds to step 420 where the basic methodology is run for a fixed number of preconditioned conjugate gradient iterations to start the imaging process and then proceeds to step 430 where the SPIOR methodology is run for several iterations. By "iteration" we mean a pass over the whole region.) The imaging process then proceeds to step 440 where the interior residual norm and the boundary error norm are computed using Equations 8(a) and/or 8(b) respectively. Once the interior residual norm and the boundary error norm have been computed, the imaging process proceeds to decision block 450 where the interior residual norm and/or the boundary error norm constitute the norm ||Solution||. If the computed value of ||Solution|| is greater than the exit norm value ||Exit||, then the process proceeds to step 430. Otherwise, if computed value of ||Solution|| is less than the exit norm value ||Exit||, the process proceeds to step 460 where the imaging process produces a graphic image of the region 200.

It should be noted that experiments have shown that the exit norm value ||Solution||, which permits the SPIOR iteration process to stop, is in the vicinity of 0.03 but this is a function of the mesh size. Alternatively, the norm may be monitored and when it begins to increase, rather than decrease, the iterative process may be stopped. However, it should be noted the exit norm value ||Solution|| may be preset to a value that has, in previous imaging procedures, generated satisfactory distinguishable images.

The process then proceeds to decision step 480 where the imaging process determines whether the current excitations should be modified to improve the graphic image of the region 200. If the imaging process decides to modify the current excitations, the process proceeds to step 470, and proceeds as outlined above. Otherwise, the process proceeds to step 490, where it ends.

Pre-Conditioned Conjugate Gradient Method

In one particular embodiment of the present invention, a Preconditioned Conjugate Gradient Method is used to initiate and, if needed, to sustain the convergence path of the SPIOR methodology. The Preconditioned Conjugate Gradient method (PCGM), which is well known in the art, is a very stable approach to the solution of systems of equations, and are described in "Methods of Conjugate Gradients for Solving Linear Systems" by M. R. Hestenes and W. Stiefel, *Journal of Research of the National Bureau of Standards*, vol. 49, no. 6, 1952, in "A Preconditioned Conjugate Gradient Method using a Sparse Linked-List Technique for the Solution of Field Problems", by Ronald L. Nakonechny, *MSc Thesis, Department of Electrical Engineering, University of Manitoba, Winnipeg, Manitoba*, Canada, 1983, in "Large Sparse Sets of Linear Equations", by J. K. Reid, Mathematics Branch, Atomic Energy Research Establishment, Harwell, England, 1971, and in "Fast Solution to Finite-Element Flow Equations by Newton Iteration and Modified Conjugate Gradient Method", by G. Gambolati, International Journal for Numerical Methods in Engineering, vol. 15, 1980, pp. 661-675.

Nakonechny (1983) describes a method to employ the preconditioned conjugate gradient method to solve the Laplace equation Neumann and Dirichlet problems. The method described by Nakonechny is a very stable and convergent method for the solution of symmetrical and positive-definite systems of linear equations. The method seeks the steepest descent method and is particularly effective when the matrix system is preconditioned in the manner described in the preceding publications. The PGCM therefore provides stability to the inventive SPIOR method and allows the inventive SPIOR method to solve the resulting nonlinear tomography system to converge rapidly while maintaining stability if the inventive SPIOR solution requires that assistance.

With reference to FIG. 4, several iterations of the Preconditioned Conjugate Gradient Method are performed at step 420 prior to the SPIOR methodology being initiated at step 430. The CGM may also be used in conjunction with the SPIOR methodology, at step 430, for further stability if required.

Zollenkopf Link-List Storage Scheme

In another embodiment, the present invention is implemented using computer software which uses a link-list storage process to store the very large sparse matrix systems produced by the method of the present invention. The link-list storage process is a sparse matrix system based on the known Zollenkopf bi-factorization method for the storage and manipulation of large systems of equations, as described in the following three references: "Bi-Factorisation—Basic Computational Algorithm and Programming Techniques", by K. Zollenkopf, "Large Sparse Sets of Linear Equations", by K. Zollenkopf, *Academic Press, London and New York*, 1971, pp. 75-96; and "The Incomplete Cholesky-Conjugate Gradient Method for the Iterative Solution of Systems of Linear Equations", by D. S. Kershaw, *Journal of Computational Physics*, vol. 26, 1978, pp. 43-65.

The present invention uses a particular integration of the CGM method with the Zollenkopf sparse storage scheme, as disclosed in the Nakonechny reference.

The following is an illustrative example of a modified Zollenkopf Link-List Storage Scheme used to implement the present invention. To illustrate the modified Zollenkopf Link-List Storage Scheme, consider the following symmetrical matrix:

$$A = \begin{bmatrix} 4 & 0 & 0 & -2 \\ 0 & 2 & -1 & -1 \\ 0 & -1 & 3 & 0 \\ -2 & -1 & 0 & 2 \end{bmatrix} \quad (13)$$

This matrix may be stored in a randomly-ordered sequence, column-wise, as shown in the following table:

TABLE 2

Matrix stored, in a lower triangular form, as a linked list.

| INDEX | CE | ITAG | LNXT | LCOL |
|---|---|---|---|---|
| 1 | 4 | 1 | 5 | 1 |
| 2 | 2 | 2 | 3 | 2 |
| 3 | -1 | 3 | 6 | 4 |
| 4 | 3 | 3 | 0 | 7 |
| 5 | -2 | 4 | 0 | |
| 6 | -1 | 4 | 0 | |
| 7 | 2 | 4 | 0 | |

The vector CE contains the matrix of coefficients stored column-wise (and not strictly in order); the parallel ITAG gives the row number of the associated entry; the parallel vector LNXT gives the location of the next position of the next column entry; and the vector LCOL (of length N) contains the location of the start of each column. An entry 0, in LNXT, signifies that no more entries exist in that column.

The above vectors contain the relevant information to reconstruct the above matrix without the storage of zero-valued matrix terms. It should be noted that the ITAG, LNXT and LCOL vectors are integer vectors, which require half the storage of a floating-point vector with the same length. When the number of unknowns becomes large, the matrix is sparsely populated with non-zero coefficients and the amount of storage required by the auxiliary vectors ITAG, LNXT and LCOL would be small by comparison. Since the matrix is symmetrical, only the lower triangular portion of the matrix is actually stored, thus reducing the amount of sparse storage by approximately half.

The advantage of implementing the present invention using the Zollenkopf storage scheme is that it is quite flexible if an additional entry is suddenly introduced. For example, consider the element A(2,1)=0 being replaced by the number −1.1, which is depicted in Table 3.

TABLE 3

The linked-list after the introduction of a new matrix entry.

| INDEX | CE | ITAG | LNXT | LCOL |
|---|---|---|---|---|
| 1 | 4 | 1 | 8* | 1 |
| 2 | 2 | 2 | 3 | 2 |
| 3 | -1 | 3 | 6 | 4 |
| 4 | 3 | 3 | 0 | 7 |
| 5 | -2 | 4 | 0 | |
| 6 | -1 | 4 | 0 | |
| 7 | 2 | 4 | 0 | |
| 8* | -1.1* | 2* | 5* | |

The addition of a matrix entry only requires changing a few pointers without re-ordering the lists. In Table 3, asterisks are added to indicate alterations made due to the introduction of new entries. The random accumulation of the system matrix is thus extremely beneficial to finite difference and finite element methods where it is usually convenient to construct the matrix in an arbitrary fashion.

Multi-Acceleration Factor (MAF) Methodology

In another embodiment of the invention, a Multi-Acceleration Factor methodology may be used to enhance the image generation process of the present invention. It was noted above that equations (10) to (12) describe the application of the acceleration to the calculation of potential change at a node 323 followed by the acceleration of conductivity calculations within finite elements 301, 302, 303, 304, 305, 306, 307 and 308.

A variety of conductivity acceleration factor values is applied to individual finite elements depending on their amplitudes or their rates of change of value. In this manner, finite elements that are changing rapidly are those likely to become part of peaks, wells, ridges, and valleys. Typically, higher conductivity acceleration $\omega_K$ factors would be applied to them rather than to those that are moving slowly. These distinctions may be made within the first few SPIOR iteration sweeps of all nodes.

The MAF method seeks out the conductivity peak values. These conductivity values are accelerated at a higher rate than the surrounding medium. Using this procedure, with inhomogeneous regions, runs the risk of latching onto stationary higher conductivity region values and needlessly accelerating them while disregarding smaller regions, of lesser conductivities, in motion, that need to be accelerated.

The MAF method uses the rate of change of the absolute value of the change of conductivity divided by the absolute value of the conductivity. This fractional conductivity change (FC) is determined on a voxel-by-voxel basis as follows:

$$FC = \frac{|\sigma^{(i+1)} - \sigma^{(i)}|}{|\sigma^{(i)}|} \quad (14)$$

where, the bracketed superscripts indicate the conductivity iteration count.

The fractional conductivity is determined dynamically and changes as the resulting image evolves. To this end, the maximum and average values (of conductivity and rate of change of conductivity with iteration) are evaluated and acceleration value transition levels are expressed as a percentage thereof. This approach is necessary as the average and maximum values change as the processing continues and normalising yields relatively constant transition level values that may be specified in advance.

For example, as shown in FIGS. 5a, 5b, 6a, and 6b, two prescribed acceleration factor values with the transition level prescribed were defined in advance. Experiments have shown that the following values of the acceleration factor to be applied to the conductivity σ within each voxel:

$$FC < 40\% \text{ set } \omega_1 = 0.2 \quad (15)$$

$$FC \geq 40\% \text{ set } \omega_2 = 1.5 \quad (16)$$

It should be noted that a person of ordinary skill in the art would readily recognize that other acceleration factors may be used.

Referring again to FIG. 3, eight nodes that have conductivity values affected by an iterative change to the potential value of a central node 323 are shown. These acceleration factor values are assigned in step 430 shown in FIG. 4 on a voxel-by-voxel basis. A method used to determine the acceleration factor transition boundary involves the calculation of the average value (of derivative with iteration count or amplitude) and then to note the difference between that value and that of the voxel in consideration.

Excitation Modification for Image Enhancement (EMIE)

In another embodiment of the invention, an Excitation Modification for Image Enhancement (EMIE) method may be used to enhance the image generation process of the present invention. The initial scanning of a body may be accomplished with a few current excitation patterns and with a significant number of voltage measurements. In a very efficient manner, the region of objects can be discerned and a decision may be made by a technician operating the apparatus of the present invention or through artificial intelligence/signature identification to enhance the quality of the image of the local region of interest. This is accomplished by adding extra excitations and/or the strength of excitations to add a weighting factor by increasing the current densities in the region of interest. In this particular embodiment of the invention, the computer 22 (FIG. 1) may include a graphical user interface (not shown) which allows a technician operating the system 1 (FIG. 1) to inject extra current excitations into an identified region of interest to enhance the quality of the image generated by the method of the present invention described above. Referring to FIGS. 5a, 5b, 5c, 5d, 6a, and 6b, the addition of localized excitations improves the shape of the imaged object. It should be noted that it is much more efficient to add localized extra excitations throughout the procedure rather than to involve a great density of excitations from the outset. It is still more efficient to add these localized excitations as the image evolves with processing.

FIGS. 5a, 5b, 5c, and 5d show conductivity amplitude plots from a simulated test in a 25 by 25 by 10 voxel region having a conductivity value of 2, the region comprising two objects having conductivities 4 and 8 respectively. The image of FIGS. 5a, 5b, 5c and 5d is shown sliced at a layer depth of 7 of 10 of the 25 by 25 by 10 voxel region. In this particular example, three current input and output pairs of electrodes are located at the middle of opposing sides of the enclosing parallelepiped. Additional current excitations are impressed at opposite walls and located in the vicinity of the initially-evolving regions of the two objects in order to enhance and accelerate convergence.

FIGS. 5a and 5c show conductivity amplitude plots for 3 current excitations and FIGS. 5b and 5d for 15 current excitations, where the present invention has been repeated for 100 iterations, and where the prescribed acceleration factor is not dynamically changing. The signal-to-noise ratio (SNR) is 60 dB. It should be noted that a Gaussian noise of 60 dB SNR, has been applied to the measurements shown in FIGS. 5a, 5b, and 5c. The effect of the noise is minimal due to the noise-resistant, least-square property of the present invention.

Referring to FIGS. 6a, 6b, 6c and 6d, conductivity amplitude and contour plots resulting from a simulated test as in FIGS. 5a, 5b, 5c and 5d is shown, however, in this example the present invention is repeated for 3,000 iterations. From FIGS. 6a and 6b, it is shown that there is a significant augmentation of current density in a region where the object being imaged is located, which in turn enhances the image quality and conductivity values result. It is apparent from the images generated during the experiments shown in FIGS. 5a, 5b, 5c, 5d, 6a, 6b, 6c and 6d, that convergence stability can be maintained by restricting high-conductivity acceleration factors to small regions within the body which are to be imaged.

The present invention permits the initial image formation to be made with few excitations, to determine regions of interest, and to increase the number of excitations as the image evolves with convergence of the procedure. For example, it is shown that three excitations sufficed at the outset in which case, the over-determination ratio was 1.08. Each excitation involves two three-dimensional field solutions, whereas voltage measurements involve minimal computational effort. Furthermore, because the matrices are very sparse, the process allows almost an unlimited number of voxels and hence permits high definition of the impedance imaging system Locator-Compensator (LC) Method In another embodiment of the invention, a Locator-Compensator method as disclosed in "An Improved Electrical Impedance Tomography (EIT) Algorithm for the Detection and Diagnosis of Early Stages of Breast Cancer", by Rajan Manicon Murugan, PhD thesis, University of Manitoba, Department of Electrical and Computer Engineering, Winnipeg, Manitoba, Canada, 1999 and U.S. Pat. No. 6,745,070 issued to A. Wexler, Z. Mu, R. M. Murugan and G. S. Strobel, 2004, may be used to advance the imaging of the discrete object or a spatially-continuous inhomogeneous admittivity region of interest. This method may be used at step 430 of FIG. 4 to calculate the current density flow patterns $\bar{J}$ through the medium and then to iterate between $\phi$ and $\sigma$ in Equation (7) while using the SPIOR methodology, thereby accelerating the convergence of the system of equations in a localized region. Should the system of equations for solving the $\phi$ and $\sigma$ values of the region not converge, then current density flow patterns $\bar{J}$ may be recalculated and the iteration procedure to calculate $\phi$ and $\sigma$ may be repeated.

This method requires that an artificial boundary surface should be constructed to enclose a region within which the conductivity distribution a is to be accurately determined by increasing the number of SPIOR iterations performed locally within this local region. To accomplish this, the current flow patterns, which emanate from the outer boundary of the region, provide the current distributions $\bar{J}$ within the reduced local region.

Immediately exterior to the region boundary, the voltages of nodes remain unchanged with iteration count and act as Dirichlet boundary conditions for the interior region solutions. Likewise, the current flow throughout the region acts as the result of Neumann boundary conditions. The solutions over the exterior region remain unchanged.

The number of SPIOR iterations, within the local region, is determined by exit criteria Equations 8(a) and 8(b) or, alternatively, by a fixed number of iterations, for example 5 to 10.

Once the local region iterations are terminated, the global solution, that is over the entire imaging region is reinvoked. This provides the current densities and boundary potentials required, by the reduced local region, for a subsequent analysis. These global and local iterations are repeated until the solutions (especially the high-and low conductivity region values) have sufficiently converged.

In this manner the object conductivity and shape converge rapidly. The computational effort involved in processing the small local regions, as described herein, is almost insignificant compared to that of the overall imaging region.

In another embodiment of the Locator-Compensator method, the artificial boundary is not required. The Multi-Acceleration Factor methodology is employed with a transition factor to determine which voxels are to be individually treated in the manner of a restricted region.

Alternatively, these currents may be used to define a continuous local and temporary Neumann boundary condition. The voltage values $\phi$ calculated at the local region boundary are temporarily fixed as Dirichlet boundary condition. Then, within this local region, the SPIOR methodology is applied iteratively to update φ, J̄ and σ. On this local boundary, the Neumann (i.e. current) boundary condition is continuous and not singular; the Dirichlet and Neumann boundary conditions may be prescribed at all points simultaneously.

Diagnostic Capability

The HDII method has the capability of producing not only images but values of conductivity as well. In general, it can yield complex-valued admittivity composed of both conductivity and susceptibility.

FIG. 7, using a simulated set of "measurements", shows the conductivities recovered with simulation model values in brackets.

Taking rapid voltage measurements, over an array of electrodes, reduces the number of three-dimensional field solutions needed in the course of image reconstruction. In conjunction with accessory algorithms, imaging can be accomplished very rapidly. The three-dimensional structure has 12 complex objects and 16 layers of voxels, i.e. 10,000 voxels. Run time was 3 minutes, on a 3 GHz laptop computer, and this will be greatly reduced with optimization and use of other auxiliary algorithms. This plot is taken at layer 15 where there are four objects. For deeply embedded objects it is necessary to employ weighting methods to ensure image quality.

Because of its ability to determine conductivity and, more generally, admittivity, HDII is clearly a diagnostic technology. It may be used to determine the state of biomedical organs, e.g. whether a breast tumour is benign or malignant as the conductivity of a malignant breast tumor is known to be double that of a benign tumour. It may not only determine the extent of geological ore lodes, it will also allow the assessment of their constituents.

Restricted-View Imaging Laboratory Test

An aluminum-covered hockey puck imaged from the top surface is shown in FIG. 8. The system was detached from a full-sized electrode array and attached to the scaled-down array shown in the photograph. The electrode array is 8×8 electrodes. Two voxels were located between pairs of adjacent electrodes and this pattern was continued at depth. Imaging was done to a depth of 6 voxel layers, which corresponds to a depth of 3 inter-electrode spacing distances resulting in 1176 voxels. The total number of linearly independent measurements, 1921, was taken. (This would be impractical for a high density system due to the large number of time-consuming three-dimensional field solutions required.) The system was overdetermined by a factor of 1921/1176≅1.6. Recovered conductivity is plotted in amplitude and with contours at 6 layers. These results were taken at iteration 35. The imaging region includes the top surface to a depth equivalent to 3 electrode-array spreads. The puck is at a depth equivalent to about two or three inter-electrode spacings. This is approximately one-half of the array dimension in depth.

If the imaging region is located within a large or infinite region the effect of the extended region needs to be catered for. For example, the extended region puts an equivalent conductivity distribution in the vicinity of the boundary of the imaging grid. Artificial truncation of the imaging grid introduces an erroneous homogeneous boundary condition into the solution of the field equations. The basic problem, we believe, is due to adding the necessary extra layers of voxels—to approximate the infinite-medium case—with a very small amount of current in those layer regions.

The equation (7) is the basic equation used for updating the conductivity distribution. If J̄ is very small, so is ∇φ and what results is a σ≅0/0 situation where the conductivity is nearly indeterminate. Where there is little current, there is little information gleaned. Almost any conductivity will then do. This means that the solution for conductivity, in such regions, is almost indeterminate. This is why, near the artificial imaging-region boundaries, one may see both peaks and very small values for σ.

A simple answer is to place read-only electrodes within the region of the extra layers (usually at the top surface, e.g. for subterranean imaging) in order to define a finite ∇φ. This will define a finite J̄ and then a defined a distribution through the iterative process. It is not advisable to inject currents through these electrodes as this will again be enforcing an artificial homogeneous-Neumann natural boundary condition at the boundary of the imaging grid (S. G. Mikhlin, Variational Methods in Mathematical Physics, Chapter III, Pergamon Press, Oxford, 1964). Some space should be left where the currents will become very small toward the outer reaches. This will ensure that the σ image recovery procedure will not produce values that are virtually indefinite.

High-Frequency and Non-Contacting Methods

Aspects of the invention may be used in other applications such as those which may be termed high-frequency and non-contacting applications. Instead of an array of electrodes, at least one transmission antenna and at least one reception antenna or an array of transmission antennas and an array or reception antennas may be used. For the contactless implementation of the invention, the mathematical aspect may be considered as follows. D. T. Paris and F. K. Hurd, in *Basic Electromagnetic Theory*, Chapter 7, McGraw-Hill, Inc., New York, 1969, pp. 304-307, 7.5 The Sinusoidal Steady State, describe the Helmholtz equations which are typically used to solve electromagnetic fields of radiating systems such as antennas. For inhomogeneous regions, they take the form of $$\nabla \times \nabla \times \bar{E} + \gamma^2 \bar{E} = -j\omega\mu \bar{J}_s \tag{17a}$$

$$\text{and } \nabla \times \nabla \times \bar{H} + \gamma^2 \bar{H} = \nabla \times \bar{J}_s \tag{17b}$$

$$\text{where } \gamma^2 = j\omega\mu(\sigma + j\omega\in) = -\omega^2 \mu \in + j\omega\mu\sigma \tag{18}$$

The $\bar{E}$ and $\bar{H}$ fields are solved numerically, e.g. by the finite element method. For convenience, and to draw a parallel with the development up to and equation (7), we refer to the solutions of (17a) and (17b) as the solutions of the Dirichlet and the Neumann problems respectively.

Note that $\bar{E}$, $\bar{H}$ and $\bar{J}$ are steady-state, sinusoidal phasor quantities and $j=\sqrt{-1}$. $\bar{J}_s$ is an applied current source. Electromagnetic waves may be launched and recorded by antennas for $\bar{E}$ and for $\bar{H}$. At conducting surfaces, the boundary conditions $\bar{E}_{tangential}=0$ and $\bar{B}_{normal}=0$ apply.

Maxwell's equations (D. T. Paris and F. K. Hurd, in *Basic Electromagnetic Theory*, Chapter 7, McGraw-Hill, Inc., New York, 1969, pp. 306) supply a constraint, in a manner similar to that of equation (3), that links the Neumann and Dirichlet solutions:

$$\nabla \times \bar{E} = -j\omega\mu\bar{H} \tag{19a}$$

$$\text{and } \nabla \times \bar{H} = (\sigma + j\omega\in)\bar{E} + \bar{J}_s \tag{19b}$$

The residuals, within the region, are therefore $$\bar{r}_1 = \nabla \times \bar{E} + j\omega\mu\bar{H} \tag{20a}$$

$$\text{and } \bar{r}_2 = \nabla \times \bar{H} - (\sigma + j\omega\delta)\bar{E} - \bar{J}_s \tag{20b}$$

To enforce compatibility, the minimization of the square of the residual over all points, for all excitations and over all finite elements is sought. It is therefore sought to minimize $$R = \sum_X \sum_j \int \int_{V_j} \int (\bar{r}_1 \cdot \bar{r}_1^* + \bar{r}_2 \cdot \bar{r}_2^*) dv \tag{21}$$

in which the residuals are employed above. This is similar to equation (5).

To seek the minimum of (21), the following differentiations are performed with $$\frac{\partial R}{\partial \sigma_i} = 0 \tag{22a}$$

$$\frac{\partial R}{\partial \epsilon_i} = 0 \tag{22b}$$

and $$\frac{\partial R}{\partial \mu_i} = 0 \tag{22c}$$

in which $\bar{H}$, $\bar{E}$ and $\bar{J}_s$ are held at previously computed values. Then $\sigma_i$, $\epsilon_i$ and $\mu_i$ may be solved as part of the iterative processes previously described.

Employing (21) and (22a), one obtains the following equation:

$$\sigma_i = \frac{-\sum_X \int \int_{V_i} \int (\nabla \times \bar{H} - \bar{J}_s) \cdot (\bar{E} + \bar{E}^*) dv}{2\sum_X \int \int_{V_i} \int \bar{E} \cdot \bar{E}^* dv} \tag{23}$$

If the source within the region $\bar{J}_s=0$, and for low frequency $\nabla \times \bar{H}=\bar{J}$ and $\bar{E}=-\nabla\phi$, then (23) reduces to (7).

With the generalization, described herein, contactless high definition impedance imaging may be accomplished.

The above contactless high definition impedance imaging may be seen as a parallel to the implementation above which uses an array of electrodes. Instead of electrodes, at least one transmission antenna may be used. Such transmission antennas produce electric and magnetic fields, the intensities of which may be detected and measured by way of at least one reception antenna. By using these antennas in place of the electrodes and by using the solutions of the Helmholtz equations (17a) and (17b) in place of the solutions to the Dirichlet and Neumann problems (where, generally, electrical field intensities correspond to voltages and magnetic field intensities correspond to currents), the same approach may be used to perform contactless high definition impedance imaging. To adapt the above method to the contactless case, it should be clear that the "body" which contains the target region to be imaged may be free space, the Earth, or any other object.

Generalization to Elasticity, Seismology and Other Physical Applications

The basic HDII method that has been introduced involving the Laplace and Poisson equations (for example, for electrostatics and low-frequency signals) for imaging and then the Helmholtz equation (for frequency-domain wave propagation) may be applied to imaging based on other physical signals. One example is the application of elasticity equations to permit imaging due, for example, to the use for seismology (for application to sub-surface imaging of contamination, definition) of ore lodes extent and richness of geophysical imaging of ore lodes.

These elasticity methods are complementary to electrical methods. The use of several such physical methods, all handled with the high definition algorithm, will yield enhanced visualization and information generally. The HDII method is therefore applicable to a variety of physical signalling means for the high-definition imaging of physical objects and inhomogeneous media.

The invention may be practiced by way of a medical machine that employs both electrical and elasticity imaging capabilities and the enhanced knowledge and diagnostic capabilities of such an instrument.

To demonstrate how the basic method can be further generalized, we consider the elasticity problem here. For example, $$\epsilon_x = \partial u / \partial x \tag{24}$$

is the unit elongation, or strain, in the x direction. u is the component of displacement in the x direction. $\tau_{xy}$ is the shearing stress component in the xy plane. Hooke's Law is given by $$\epsilon_x = \sigma_x / E \tag{25}$$

where E is the modulus of elasticity. The resulting lateral strain components are $$\epsilon_z = -v\sigma_x / E \tag{26}$$

and $$\epsilon_y = -v\sigma_x / E \tag{27}$$

in which v is the Poisson's ratio constant. Equations (24) to (27) are fully described and generalized in S. P. Timoshenko and J. N. Goodier, Theory of Elasticity, McGraw-Hill Book Company, Copyright 1934, 1970, Chapter 1, p. 8. ISBN 07-064720-8

Note tha parallel of (24) to (27) with Ohm's Law Eqn. (3).

For the following, please refer to O. C. Zienkiewicz, The Finite Element Method in Engineering Science, McGraw-Hill Publishing Company Limited, copyright 1971, Chapters 1 and 6.

Zienkiewicz describes the finite element method construction of the sparse matrix equation $$\{f\} = [K]\{\delta\} \tag{28}$$

in which $\{f\}$ and $\{\delta\}$ are column matrices of forces and displacements respectively and $[K]$ is the sparse stiffness matrix.

To apply the HDII method, the system is solved for a number of applied force configurations and the resulting displacements are measured. This is similar to the Neumann and Dirichlet boundary conditions of the low-frequency case. These field solutions yield the interior solution values to which Hook's Law is applied over all of the nodes and the modulus of elasticity and Poisson's ratio are evaluated, within all finite elements, in a least-square manner as is described in equations (7) and (23). The matrix sparsity is retained.

Implementation of Invention to Elasticity and Seismology Cases

In seismology the parallel to the driver is typically referred to as the transmitter or the energy source. At other measurement points, the acoustic signal strength would be measured by a receiver, frequently a geophone. In the application of elasticity theory, to a somewhat rigid body, the driver would be an applied force. This is a parallel to the electrical current source. A displacement, located elsewhere, would be measured by a receiver. This is the equivalent of the voltage measured at other points. Devices are available for these measurements [R. E. Sheriff and L. P. Geldart, Exploration Seismology, Cambridge University Press, 1999. ISBN 0 521 46282 7 hardback and ISBN 0 521 462826 4 paperback].

With the understanding of the above, FIG. 1 may be interpreted to represent the seismology and elasticity etc. applications. For example, the Current Driver would be interpreted as the Driver and the Current Sensor would be the Sensor, the Electrode Array would be the Driver and Sensor Array, and so on. The methods described above would still hold.

Embodiments of the invention may be implemented in any conventional computer programming language. For example, preferred embodiments may be implemented in a procedural programming language (e.g. "C") or an object oriented language (e.g. "C++"). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server over the network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

It should be understood that the preferred embodiments mentioned here are merely illustrative of the present invention. Numerous variations in design and use of the present invention may be contemplated in view of the following claims without straying from the intended scope and field of the invention herein disclosed.

The embodiments of the invention in which an exclusive property or privilege is claimed as defined as follows:

1. A method of impedance imaging of a target region located within a body, the method comprising the steps of:
    (a) representing the body as a plurality of adjacent finite elements, each finite element having a plurality of nodes and a distribution of admittivity values at a set of pre-defined points therein;
    (b) applying at least one electrical current, at at least one selected current input electrode, to flow within the body and exit therefrom at at least one selected current output electrode;
    (c) measuring at least one voltage at one or both of the at least one selected current input electrode and current output electrode;
    (d) identifying a measured voltage group of nodes as comprising those nodes corresponding to the at least one selected current input or current output electrode;
    (e) identifying a volume comprising a first one of the finite elements and those finite elements defining a region thereround, wherein the first one of the finite elements is selected based on the rate of change of the distribution of admittivities;
    (f) calculating at least one first voltage value, for each node that lies within the volume and outside the measured voltage group of nodes from the measured voltages at the measured voltage group of nodes;
    (g) calculating at least one second voltage value for each node that lies within the volume from the distribution of admittivity values and the at least one electrical current;
    (h) deriving a current value corresponding to each pre-defined point within the volume from the corresponding distribution of admittivity values and the at least one second voltage value;
    (i) updating the distribution of admittivity values corresponding to the set of pre-defined points within each finite element within the volume from the corresponding current value, the at least one first voltage value and the measured voltages at those of the measured voltage group of nodes that lie within the volume; and
    (j) displaying an image of the target region using the distribution of admittivity values within the body.

2. A method according to claim 1, wherein the target region is selected from at least one member of the group consisting a discrete object and a spatially-continuous inhomogeneous admittivity region.

3. A method according to claim 1, wherein the step of representing comprises initializing the distribution of admittivity values to arbitrary values.

4. A method according to claim 1, wherein the step of applying comprises ensuring that a total current sum of the at least one electrical current equals zero.

5. A method according to claim 1, wherein the step of applying at least one electrical current comprises applying the selected current input electrodes to the surface of the body.

6. A method according to claim 1, wherein the step of applying at least one electrical current comprises inserting the selected current input electrodes within the body.

7. A method according to claim 1, wherein the step of measuring comprises measuring the at least one voltage with respect to a voltage reference point through which no current flows.

8. A method according to claim 1, wherein the step of measuring comprises positioning each selected voltage electrode remotely from each selected current input electrode.

9. A method according to claim 1, wherein the step of measuring comprises positioning each selected voltage electrode remotely from each selected current output electrode.

10. A method according to claim 1, wherein the step of measuring comprises applying the at least one selected voltage electrode to the surface of the body.

11. A method according to claim 1, wherein the step of measuring comprises inserting the at least one selected voltage electrode within the body.

12. A method according to claim 1, wherein the step of identifying comprises selecting the region to include those finite elements which are affected by changes to a node within the selected finite element.

13. A method according to claim 1, wherein the step of identifying comprises selecting the region to include those finite elements contiguous with the selected finite element.

14. A method according to claim 1, wherein the step of calculating at least one first voltage value comprises applying at least one measured voltage of the measured voltage group of nodes as a Dirichlet boundary condition.

15. A method according to claim 1, wherein the step of calculating at least one second voltage value comprises applying the distribution of conductivities of the volume against at least one of the applied electrical currents as a Neumann boundary condition.

16. A method according to claim 1, wherein the step of applying the distribution of conductivities comprises applying the distribution as a Poisson distribution.

17. A method according to claim 1, wherein the step of applying the distribution of conductivities comprises applying the distribution as a Laplace distribution.

18. A method according to claim 1, wherein, before step (j), steps (b) and (c) are repeated at at least one different location and thereafter steps (e) through (i) are repeated using the new at least one voltage.

19. A method of impedance imaging of a target region located within a body, the method comprising the steps of:
- (a) representing the body as a plurality of adjacent finite elements, each finite element having a plurality of nodes and a distribution of admittivity values at a set of pre-defined points therein;
- (b) applying at least one electrical current, at at least one selected current input electrode, to flow within the body and exit therefrom at at least one selected current output electrode;
- (c) measuring at least one voltage at one or both of the at least one selected current input electrode and current output electrode;
- (d) identifying a measured voltage group of nodes as comprising those nodes corresponding to the at least one selected current input or current output electrode;
- (e) identifying a volume comprising a first one of the finite elements and those finite elements defining a region therearound;
- (f) calculating at least one first voltage value, for each node that lies within the volume and outside the measured voltage group of nodes from the measured voltages at the measured voltage group of nodes;
- (g) calculating at least one second voltage value for each node that lies within the volume from the distribution of admittivity values and the at least one electrical current;
- (h) deriving a current value corresponding to each pre-defined point within the volume from the corresponding distribution of admittivity values and the at least one second voltage value;
- (i) updating the distribution of admittivity values corresponding to the set of pre-defined points within each finite element within the volume from the corresponding current value, the at least one first voltage value and the measured voltages at those of the measured voltage group of nodes that lie within the volume;
- (ia) identifying a second volume comprising a second one of the finite elements not previously selected, and those finite elements defining a region therearound;
- (ib) repeating steps (f) through (i) in respect of the second volume;
- (ic) repeating steps (ia) and (ib) until an exit norm is Satisfied; and
- (j) displaying an image of the target region using the distribution of admittivity values within the body.

20. A method of impedance imaging of a target region located within a body, the method comprising the steps of:
- (a) representing the body as a plurality of adjacent finite elements, each finite element having a plurality of nodes and a distribution of admittivity values at a set of pre-defined points therein;
- (b) applying at least one electrical current, at at least one selected current input electrode, to flow within the body and exit therefrom at at least one selected current output electrode;
- (c) measuring at least one voltage at one or both of the at least one selected current input electrode and current output electrode;
- (d) identifying a measured voltage group of nodes as comprising those nodes corresponding to the at least one selected current input or current output electrode;
- (d1) initializing the distribution of admittivity values for each finite element to a pre-determined value;
- (d2) calculating at least one third voltage value for each node of each finite element from the at least one measured voltage of the measured voltage group of nodes;
- (d3) calculating at least one fourth voltage value for each node of each finite element from the distribution of admittivity values and the at least one electrical current;
- (d4) deriving a second current value corresponding to each pre-defined point within each finite element from the pre-determined distribution of admittivity values and the at least one fourth voltage value;
- (d5) updating the distribution of admittivity values corresponding to the set of pre-defined points within each finite element from the corresponding second current value, the at least one third voltage value and the measured voltages;
- (e) identifying a volume comprising a first one of the finite elements and those finite elements defining a region therearound;
- (f) calculating at least one first voltage value, for each node that lies within the volume and outside the measured voltage group of nodes from the measured voltages at the measured voltage group of nodes;
- (g) calculating at least one second voltage value for each node that lies within the volume from the distribution of admittivity values and the at least one electrical current;
- (h) deriving a current value corresponding to each pre-defined point within the volume from the corresponding distribution of admittivity values and the at least one second voltage value;
- (i) updating the distribution of admittivity values corresponding to the set of pre-defined points within each finite element within the volume from the corresponding current value, the at least one first voltage value and the measured voltages at those of the measured voltage group of nodes that lie within the volume; and
- (j) displaying an image of the target region using the distribution of admittivity values within the body.

21. A method of impedance imaging of a target region located within a body, the method comprising the steps of:
- (a) representing the body as a plurality of adjacent finite elements, each finite element having a plurality of nodes and a distribution of admittivity values at a set of pre-defined points therein;
- (b) applying at least one electrical current, at at least one selected current input electrode, to flow within the body and exit therefrom at at least one selected current output electrode;

(c) measuring at least one voltage at one or both of the at least one selected current input electrode and current output electrode;
(d) identifying a measured voltage group of nodes as comprising those nodes corresponding to the at least one selected current input or current output electrode;
(e) identifying a volume comprising a first one of the finite elements and those finite elements defining a region therearound;
(f) calculating at least one first voltage value, for each node that lies within the volume and outside the measured voltage group of nodes from the measured voltages at the measured voltage group of nodes;
(g) calculating at least one second voltage value for each node that lies within the volume from the distribution of admittivity values and the at least one electrical current;
(h) deriving a current value corresponding to each pre-defined point within the volume from the corresponding distribution of admittivity values and the at least one second voltage value;
(i) updating the distribution of admittivity values corresponding to the set of pre-defined points within each finite element within the volume from the corresponding current value, the at least one first voltage value and the measured voltages at those of the measured voltage group of nodes that lie within the volume, and further assigning a pre-determined distribution of admittivity values corresponding to the set of pre-defined points within each finite element within the volume, based on a difference between the new admittivity values and the previous admittivity value; and
(j) displaying an image of the target region using the distribution of admittivity values within the body.

22. A method according to claim 21, further comprising before step (j) the steps of:
(i1) identifying a second volume comprising a second one of the finite elements not previously selected, and those finite elements defining a region therearound, based on the difference between the new admittivity value and the previous admittivity value; and
(i2) applying at least one electrical current, at at least one of the current input electrodes within the second volume, to flow within the body and exit therefrom at at least one of the current output electrodes within the second volume.

* * * * *

UNITED STATES PATENT AND TRADEMARK OFFICE
CERTIFICATE OF CORRECTION

PATENT NO. : 8,369,941 B2  Page 1 of 1
APPLICATION NO. : 12/375145
DATED : February 5, 2013
INVENTOR(S) : Wexler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this
First Day of September, 2015

Michelle K. Lee
*Director of the United States Patent and Trademark Office*